United States Patent
Stott et al.

(10) Patent No.: US 8,597,920 B2
(45) Date of Patent: Dec. 3, 2013

(54) **CLASS OF *CHLOROFLEXI*-LIKE THERMOPHILIC CELLULOSE DEGRADING BACTERIA**

(75) Inventors: Matthew Bryan Stott, Taupo (NZ); Peter Franklin Dunfield, Calgary (CA); Michelle Anne Crowe, Taupo (NZ)

(73) Assignee: Institute Of Geological And Nuclear Sciences Limited (NZ)

( * ) Notice: Subject to any disclaimer, the term of this patent is extended or adjusted under 35 U.S.C. 154(b) by 254 days.

(21) Appl. No.: 12/920,280

(22) PCT Filed: Mar. 11, 2009

(86) PCT No.: PCT/NZ2009/000034
§ 371 (c)(1),
(2), (4) Date: Nov. 29, 2010

(87) PCT Pub. No.: WO2009/113882
PCT Pub. Date: Sep. 17, 2009

(65) Prior Publication Data
US 2011/0091951 A1   Apr. 21, 2011

Related U.S. Application Data

(60) Provisional application No. 61/035,414, filed on Mar. 11, 2008.

(51) Int. Cl.
*C12P 7/10* (2006.01)

(52) U.S. Cl.
USPC ........................................................ 435/165

(58) Field of Classification Search
USPC ........................................................ 435/165
See application file for complete search history.

(56) References Cited

U.S. PATENT DOCUMENTS

| 4,510,243 A | 4/1985 | Haga et al. |
| 5,698,429 A | 12/1997 | Dees |
| 5,958,758 A | 9/1999 | Miller et al. |

FOREIGN PATENT DOCUMENTS

WO   WO-97/10352 A1   3/1997

OTHER PUBLICATIONS

Accession No. DQ395967 (2006).*
"*Chloroflexi* bacterium P352 partial 16S rRNA gene, isolate P352", GenBank Accession No. AM749769, (2008), 1 pg.
"*Chloroflexi* bacterium P359 partial 16S rRNA gene, isolate P359", GenBank Accession No. AM749770, (2008), 1 pg.
"*Chloroflexi* bacterium T104 partial 16S rRNA gene, isolate T104", GenBank Accession No. AM749781, (2008), 1 pg.
"*Chloroflexi* bacterium T81 partial 16S rRNA gene, isolate T81", GenBank Accession No. AM749782, (2008), 1 pg.
"International Application Serial No. PCT/NZ2009/000034, International Search Report mailed May 27, 2009", 5 pgs.
"International Application Serial No. PCT/NZ2009/000034, Written Opinion mailed May 27, 2009", 6 pgs.
"Uncultured *Chloroflexi* bacterium partial 16S rRNA gene, clone Wkt_02", GenBank Accession No. AM749737, (2008), 1 pg.

* cited by examiner

*Primary Examiner* — Tekchand Saidha
(74) *Attorney, Agent, or Firm* — Schwegman Lundberg & Woessner, P.A.

(57) ABSTRACT

The present invention relates to a new class of Chloroflexi-like bacteria. The bacteria are thermophilic cellulose degrading bacteria. Compositions and methods for degrading cellulose using the Chloroflexi-like bacteria are also provided.

12 Claims, 16 Drawing Sheets

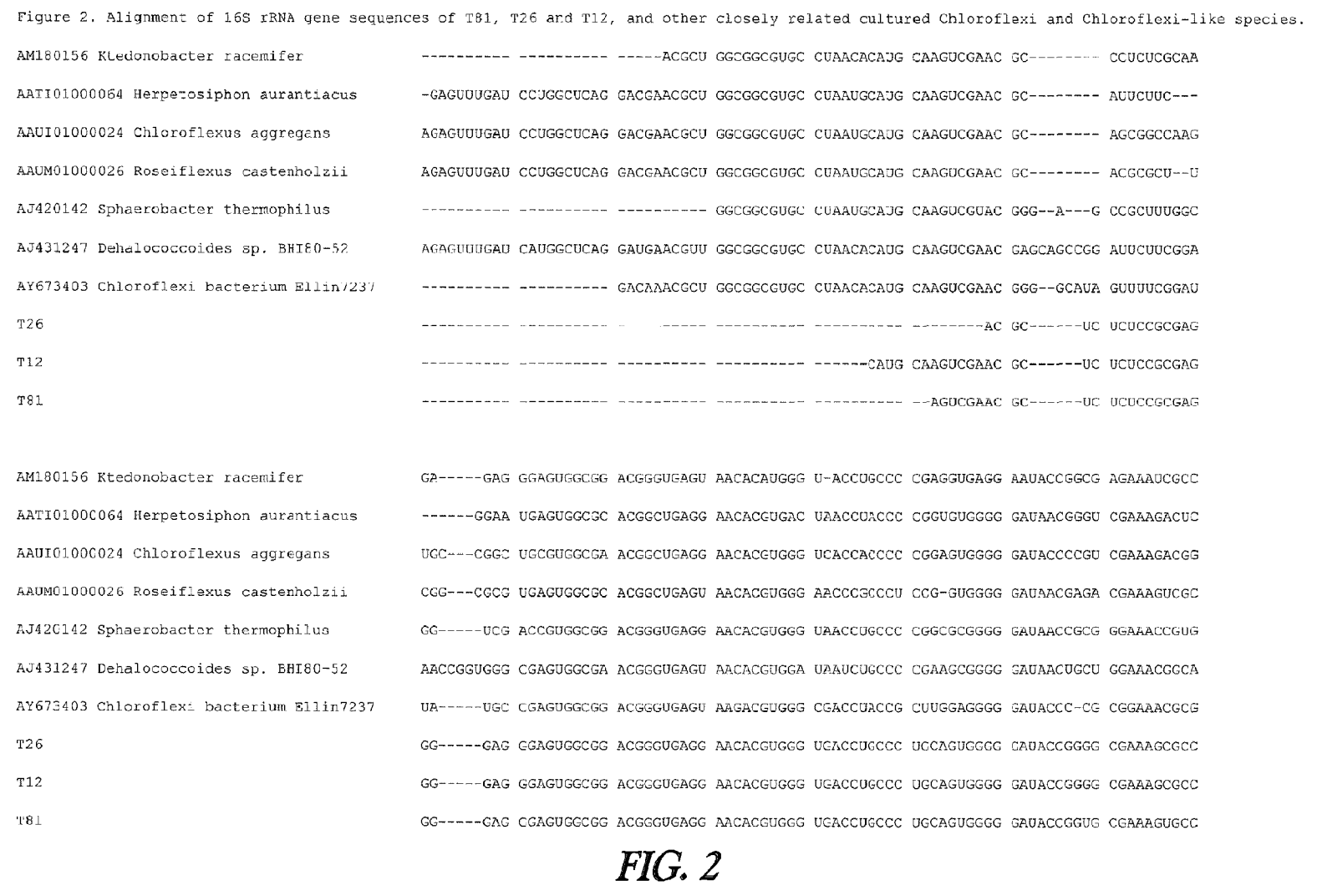

Figure 2. Alignment of 16S rRNA gene sequences of T81, T26 and T12, and other closely related cultured Chloroflexi and Chloroflexi-like species.

FIG. 2

| | | | | | | |
|---|---|---|---|---|---|---|
| AM180156 Ktedonobacter racemifer | G-ACAAUACC | GCAUAUGUUC | CUCCCGG--- | -------A | ACAAAGCU-- | -CGCAAGGGC | -CCCUUGGG- | -------AU |
| AATI01000064 Herpetosiphon aurantiacus | G-CUAAUCCC | GCAUACGAUC | CGCCUCGGCG | G-------- | GGAAAGC--- | --CGCAAGGC | -GCACUGG-- | -------GCG |
| AAUI01000024 Chloroflexus aggregans | G-ACAAUCCC | GCAUACG--- | ---CUCUACG | G-------A | GGAAAGC--- | --CAUACGGC | -GCUCCGG-- | -------GAC |
| AAUM01000026 Roseiflexus castenholzii | G-CUAAUCCC | GCAUACG--- | ---UCCGCAA | G-------G | GGAAAGC--- | --GCCUGGGC | -GCGCCGGA- | -------GGAG |
| AJ420142 Sphaerobacter thermophilus | G-CUAAUACC | CCAUGGCUC | GGUGGGGGU | GACCUGAUCG | AGCAAAG--- | -GCGAAAGC | CGUCCGGG- | -------AG |
| AJ431247 Dehalococcoides sp. BHI80-52 | G-CUAAUACC | GCAUGUGCUU | GCCGAUCGG | A---UGUCU | CGUAACUAAA | --GCUUUGGC | -GCUUCGGG- | -------AG |
| AY673403 Chloroflexi bacterium Ellin7237 | GGAUAAGACC | GCAUACCCUG | AUCUGGGUAG | AUCCGGAUCA | GGAAAAC--- | --GCCAGAGC | -GUGCCAAGU | G-------AG |
| T26 | G-ACAAUCCC | GCAUACGGUG | GCGUCUUGCG | AGAGGCGCCA | GGAAAGCUUC | CJGCCGGAGG | -GUGGGAGGC | GCUGCAGGAG |
| T12 | G-ACAAUCCC | GCAUACGGUG | GCGUCUUCCG | AGAGGCGCCA | GGAAAGCUUY | CYGCCGGAGG | -GCGGGAGGC | GCUGCAGGAG |
| T81 | G-ACAAUCCC | GCAUACGGUG | GCGUCUUUGCG | AGAGGCGCCA | GGAAAGCUUC | CUGCCGGAGG | -GUGGAGGC | GCUGCAGGAG |
| | | | | | | | |
| AM180156 Ktedonobacter racemifer | GGGCCUGUGG | CCGAUUAGCU | UGUUGGUGAG | GUAAGAGCUU | ACCAAGGCCA | CGAUCGGUAG | CUGGUCUGAG | AGGAUGUCA |
| AATI01000064 Herpetosiphon aurantiacus | GGGGUCGCGU | CCCAUUAGAU | AGUUGGUGUG | GUAACGGCGC | ACCAACUCCA | UGAUGGGUCU | CUGGUCUGAG | AGGACGACCA |
| AAUI01000024 Chloroflexus aggregans | GGGCCUGCGG | CCCACUCAGGU | AGUUGGUGUG | GUAACGGCGC | ACCAAGCCAC | UGACGGGUAC | CCGGUCUGAG | AGGACGCCG |
| AAUM01000026 Roseiflexus castenholzii | GGGCCUGCGG | CCCAUCAGGU | AGUUGGUGG | GUAACGGCCC | ACCAAGCCGA | UGACGGGUAG | CUGGUCUGGG | AGGAUGACCA |
| AJ420142 Sphaerobacter thermophilus | GGGCCUGCGG | CCUAUCAGCU | AGACGGUGGG | GUAAUGGCCU | ACGUGGGGA | UGACGGGUAG | CUGGUCUGAG | AGGACGAUCA |
| AJ431247 Dehalococcoides sp. BHI80-52 | GAGUCCGCGG | CCGAUUAGCU | AGUUGGCCAG | GUAAUGGCUC | ACCAAGGCCA | UGAUCCGGUAG | GGGCGGGUAG | AGCGUGACCC |
| AY673403 Chloroflexi bacterium Ellin7237 | GGGCCUGCGG | CCGAUUAGCU | AGUUGGGGGG | GUAACGCGCU | CCCAAGGCCG | GUAACGCGGA | CUGGUCUCAG | AGGACGAUCA |
| T26 | GGGCCUGCGC | CCGAUUAGCU | AGUUGGUAGG | GUAAUGGCCU | ACCAAGGCGA | CGAUCGGUAG | CUGGUCUGAG | AGGACGAUCA |
| T12 | GGGCCUGCGC | CCGAUUAGCU | AGUUGGUAGG | GUAAUGGCCU | ACCAAGGCGA | CGAUCGGUAG | CUGGUCUGAG | AGGACGAUCA |
| T81 | GGGCCUGCGC | CCGAUUAGCU | GGUUGGUAGG | GUAAAGGCCU | ACCAAGGCGA | CGAUCGGUAG | CUGGUCUGAG | AGGACGAUCA |

*FIG. 2 (CONT.)*

| | | | | | | |
|---|---|---|---|---|---|---|
| AM180156 Ktedonobacter racemifer | GCCACACUGG | GAUUGAGA-A | CGGCCCAGAC | UCCUACGGGG | GGCAGCAGUG | AGGAAUUUUC | GUCAAUGGGG | GCAACCCUGA |
| AATI01000064 Herpetosiphon aurantiacus | GACAGAUUGG | GACUGAGACA | CGGCCCAAAC | UCCUACGGGG | GGCAGCAGCA | AGGAAUUUUC | GGCAAUGGGC | GCAAGCCUGA |
| AAUI01000024 Chloroflexus aggregans | GGCAGACUGG | GACUGAGACA | CGGCCCAGAC | UCCUACGGGA | GGCAGCAGCA | AGGAAUUUUC | CCCAAUGGGC | ACACCCCUGA |
| AAUM01000026 Roseiflexus castenholzii | GCCAGACUGG | GACUGAGACA | CGGCCCCGAC | UCCUACGGGA | GGCACCAGCA | AGGAAUUUUC | GGCAAUGGGC | GCAAGCCUGA |
| AJ420142 Sphaerobacter thermophilus | GCCACACUGG | GACUGAGACA | CGGCCCCGAC | UCCUACGGGA | GGCACCAGCA | AGGAAUUUUC | CGCAAUGGGC | GCAAGCCUGA |
| AJ431247 Dehalococcoides sp. BHI80-52 | CCCACACUGG | AACUGAGACA | CGGUCCUGAC | UCCUACGGGG | GGCAGCAGUG | AGGAUAUUG | CACAAUGGGC | GAAAGCCUGA |
| AY673403 Chloroflexi bacterium Ellin7237 | GCCACACUGG | GAUUGAGA-A | CGGCCCAGAC | UCCUACGGGG | GGCACCAGUG | AGGGAUCUUC | GGCAAUGGGG | GAAACCCUGA |
| T26 | GCCACACUGG | GAUUGAGAGA | CGGCCCCAGAC | UCCUACGGGG | GGCACCAGUG | AGGGAUCUUC | GGCAAUGGGU | GAAAGCCUGA |
| T12 | GCCACACUGG | GAUUGAGAGA | CGGCCCAGAC | UCCUACGGGG | GGCAGCAGUG | AGGGAUCUUC | GGCAAUGGGC | GAAAGCCUGA |
| T81 | GCCACACUGG | GAUUGAGAGA | CGGCCCAGAC | UCCUACGGGG | GGCAGCAGUG | AGGGAUCUUC | GGCAAUGGGC | GAAAGCCUGA |
| | | | | | | | |
| AM180156 Ktedonobacter racemifer | ACGAGCAACG | CCGGCGUGCAG | GAGGACGCUU | UUCGGAGUGU | AAACUGCUUU | UCUUGGGGAC | GAGUAAGG-- | ACGUACCYA |
| AATI01000064 Herpetosiphon aurantiacus | CCGAGCAACG | CCGGCGUGGAG | GAUGACGGCU | CUUGGGUUGU | AAACUCCUUU | UGGGGGGGAC | GAUAAUGA-- | -CGGUACCCU |
| AAUI01000024 Chloroflexus aggregans | GGGAGCAACG | CCGGCGUGGAG | GACGACGGCC | UUCGGGUUGU | AAACUCCCUU | CGGGUGGGAC | GAGACUGA-- | -CGGUACCAC |
| AAUM01000026 Roseiflexus castenholzii | CCGAGCAACG | CCGGCGUGCGG | GAUGACGGCC | UUCGGGUUGU | AAACCGCUUU | UCGGGGGGAC | GACUACGA-- | -CGGUACCCC |
| AJ420142 Sphaerobacter thermophilus | CGGAGCGACG | CCGGCGUGGAG | GAUGACGCCC | UUCGGGUUGU | AAACUCCUUU | UCGGGGGGAC | GAAGGCAGUG | ACGGUACCCC |
| AJ431247 Dehalococcoides sp. BHI80-52 | UGCAGCAACG | CCGGCGUGGG | GAUGAAGGCC | UUCGGGUUGU | AAACCCCCUU | UCUGCGGGAA | GAGAAAGG-- | ACGGUACCGC |
| AY673403 Chloroflexi bacterium Ellin7237 | CCGAGCGACG | CCGGCGUGCGG | GACGAAGGCC | UUCGGGUUGU | AAACCGCUUU | UCUUGGGGAC | GAGAAUGG-- | ACGGUACCCG |
| T26 | CCGAGCGACG | CCGGCGUGCAG | GAAGAAGGCC | UUCGGGUUGU | AAACUGCUUU | UCUGGGGGAA | GAGGGAGG-- | ACGUACCCC |
| T12 | CCGAGCGACG | CCGGCGUUCAG | GAAGAAGGCC | UUCGGGUUGU | AAACUGCUUU | UCUGGGGGAA | GAGGGAGG-- | ACGUACCCC |
| T81 | CCGAGCGACG | CCGGCGUGCAG | GAAGAAGGCC | UUCGGGUUGU | AAACUGCUUU | UCUGGGGGAA | GAGAGAGG-- | ACGUACCCC |

*FIG. 2 (CONT.)*

| | | | | | | |
|---|---|---|---|---|---|---|
| AM180156 Ktedonobacter racemifer | AGGAUAAGC | CCCGGCUAAC | UACGUGCCAG | CAGCCGCGGU | AAUACGUAGG | GGGCAAGCGU | UGUCCGGAGU | UAUU-GGGCG |
| AATI01000064 Herpetosiphon aurantiacus | CCGAAUCAGG | CCCGGCUAAC | UACGUGCCAG | CAGCCGCGGU | AAUACCUAGG | GGCCAAGCGU | UGUCCGGAAU | UACU-GGGCG |
| AAUI01000024 Chloroflexus aggregans | CACAAGCAGC | CCCGGCUAAC | UCUGUGCCAG | CAGCCGCGGU | AAGACAGAGG | GGGCAAGCGU | UGUCCGGAGU | UACU-GGGCG |
| AAUM01000026 Roseiflexus castenholzii | CGGAAGAAGC | CCCGGCUAAC | UCUGUGCCAG | CAGCCGCGGU | AAGACAGAGG | GGGCAGCGU | UGUCCGGAGU | UACU-GGGCG |
| AJ420142 Sphaerobacter thermophilus | CGGAAGAAGC | ACCGGCUAAC | UACGUGCCAG | CAGCCGCGGU | AAGACGUAGG | GUGCGAGCGU | UGUCCGGAGU | UACU-GGGCG |
| AJ431247 Dehalococcoides sp. BHI80-52 | AGGAUAAGU | CUCGGCUAAC | UACGUGCCAG | CAGCCGCGGU | AAACCUACC | ACCCCAACGU | UAUCCGGAGU | UACUGGGCG |
| AY673403 Chloroflexi bacterium Ellin7237 | AGGAAGAAGC | CUCGGCUAAC | UACGUGCCAG | CAGCCGCGGU | AAUACGUAGG | AGGCGAGCGU | UGUCCGGAGU | UACU-GGGCG |
| T26 | AGGAAGAACC | CCCGGCAAAC | UACGUGCCAG | CAGCCGCGGU | AAGACGUAGG | GGGCGAGCGU | UGUCCGGAGU | UACU-GGGCG |
| T12 | AGGAAGAAGC | CCCGGCAAAC | UACGUGCCAG | CAGCCGCGGU | AAGACGUAGG | GGGCGAGCGU | UGUCCGGAGU | UACU-GGGCG |
| T81 | AGGAAGAAGC | CCCGGCAAAC | UACGUGCCAG | CAGCCGCGGU | AAGACGUAGG | GGGCGAGCGU | UGUCCGGAGU | UACU-GGGCG |
| | | | | | | | | |
| AM180156 Ktedonobacter racemifer | UAAAGCGCAC | GCAGGCGGUU | UCGUACGUCC | GGAGUGACAG | UUCCCGGCUC | AACUGGGAAA | GGUCUCCGGA | A-ACGGCCAG |
| AATI01000064 Herpetosiphon aurantiacus | UAAAGCGUGG | GUAGGCGGUC | GAUGAUGUGC | CGCGUGAAAG | CGCCGAGUA | AUGCCGGCGA | GGUCCCCCUA | C-ACACGUUG |
| AAUI01000024 Chloroflexus aggregans | UAAAGGGCGC | GGAGGCGGUC | UGCUCCGCUC | GCGCUGAAAG | CGCCCCGCUU | AACGGGGCGA | GG-CGCCCCG | AUACGAGCAG |
| AAUM01000026 Roseiflexus castenholzii | UAAAGCGCGC | GCAGGCGGUG | GUCUCAGUGU | CGUGUGAAAG | CCCCGGCUC | AACCGGGGAG | GGUCAUGGCA | A-ACUAGACG |
| AJ420142 Sphaerobacter thermophilus | UAAAGGGCGC | GUAGGCGGCU | GCCCGCGCG | CACGUGAAAG | CCCCGGCUC | AACCGGGGAG | GGUCGUGCGA | G-ACGGGGUG |
| AJ431247 Dehalococcoides sp. BHI80-52 | UAAAGCGCUC | GCAGGCGGCU | UCGUAAGUCU | CAUGUGAAAG | CCCCGGCUU | AACUGGGGAA | GGCCAUUGGA | U-ACUGCGGA |
| AY673403 Chloroflexi bacterium Ellin7237 | UAAAGGGUGC | GUAGGCGCU | GCGCCGUGG | AGGGUCGAAAU | CUCUCGGCUU | ACCCGGGAGG | GGGCUUUCCA | G-ACGGCCUG |
| T26 | UAAAGGGCCU | GUAGGCGGUC | GGGCAGGUU | CGGCGGACAG | CCCCGGCUU | CACUCCGGGA | GAAGCACCAA | G-ACGGUCCG |
| T12 | UAAAGGGCCU | GUAGGCGGUC | GGGCAGGUU | GGGCAGGACAG | CCCGCGCUU | CACUCGGGGA | GAAGCAGGAA | G-ACGGCCCG |
| T81 | UAAAGGGCCU | CUACCCGGUC | GGGCAGGUU | CGGCGGACAG | CCCGCGGCUU | CACUCGGGGA | GCAGCAGGAA | G-ACGGCUCG |

*FIG. 2 (CONT.)*

| | | | | | |
|---|---|---|---|---|---|
| AM180156 Ktedonobacter racemifer | ACUUGAGGGC | UUCAGAGGGA | CACCGAAUUC | CGGGUGGAGU | GGUGAAAUGC GUAGAGAUCC GGAGGAACAC CAAUGGGCGAA |
| AATI01000064 Herpetosiphon aurantiacus | ACUAGAGGCU | CGCAGAGGAA | CGUGGAAUUC | CCGGUGUAGU | GGUGAAAUGC GUAGAUAUCG GGAGGAACAC CAGUGGCGCA |
| AAUI01000024 Chloroflexus aggregans | GCUGGAGCCG | AGCAGAGGGU | GGUGGAAUUC | CCCCUCGAGC | GGUGAAAUGC GUAGAGAUCC GGAGGAACGC CGGUGAGCA |
| AAUM01000026 Roseiflexus castenholzii | ACUAGAGCGG | CGGAGAGGCC | CCUCGAAUUG | CCGGUGUAGC | GGUGAAAUGC GCAGAGAUCG CAAGGGGAA |
| AJ420142 Sphaerobacter thermophilus | CCUACAGGCA | GGGAGAGGCU | GGUGGAAUUC | CCGGUGUAGC | GGUGAAAUGC GGAGGAACAC CGGUGGCGAA |
| AJ431247 Dehalococcoides sp. BHI80-52 | GCUUGAGGAC | AGGAGAGGAA | AGUGGAAUUC | CCGGUGUAGC | GGUGGAAUGC GUAGAUAUCG GGAGGAACUC CAGUGGCGAA |
| AY673403 Chloroflexi bacterium Ellin7237 | GCUUGAGGGA | CGGAGAGGGG | CGUGGAAUUC | CGGGUGUAGC | GGUGAAAUGC GGAGGAACAC CGACGCGUA |
| T25 | ACUUGAGGGC | CACAGAGGGA | CAUGGAAUUC | CCGGUGAGC | GGUGAAAUGC GUAGAGAUCG GGAAGAACAC CGAAGGCGAA |
| T12 | ACUUGAGGGC | CACAGAGGGA | SAUGGAAUUC | CCGGUGAGC | GGUGAAAUGC GGAAGAACAC CGAACGCCAA |
| T81 | ACUUGAGGGC | CACAGAGGGA | CAUGGAAUUC | CCGGUGAGC | GUCAAAUCC GGAAGAACAC CGAAGGCGAA |
| | | | | | |
| AM180156 Ktedonobacter racemifer | GGCAGUGUCC | UGGAAGCAU | CUGACGCUCA | GGUGCGAAAG | CUAGGGGAGC GAACAGGAUU AGAUACCCUG GUAGUCCUAG |
| AATI01000064 Herpetosiphon aurantiacus | AGCGGCGUUC | UGGGCGAGAC | CUGACACUGA | GCCACACGG | CGUGGGAGC AAACAGGAUU AGAUACCCUG GUAGUCCACG |
| AAUI01000024 Chloroflexus aggregans | GUCGGCCACC | UGGGCUCGAC | CUGACGCUGC | GCCGCCACCG | CGUCGGGAGC AAACCGGAUU AGAUACCCGG GUAGUCCACG |
| AAUM01000026 Roseiflexus castenholzii | GCCAGGGGGC | UGGGCCGCUGG | CUGACGCUGA | GGCGCGACAG | CGUCGGGAGC AAACCGGAUU AGAUACCCGG GUAGUCCACG |
| AJ420142 Sphaerobacter thermophilus | GGCGGCCAGC | UGGCCCUGAC | CUGACGCUGA | GGCGCGAAGG | CGCGGGGAGC GAACGGGAUU AGAUACCCCG GUAGUCCCG |
| AJ431247 Dehalococcoides sp. BHI80-52 | GGCGACUUUC | UGGCCUGUUC | CUGACGCUCA | GGAGCGAAAG | CGUGGGAGC CAACAGGAUU AGAUACCCUG GUAGUCCACG |
| AY673403 Chloroflexi bacterium Ellin7237 | GCCAGCCCCC | UGGCCGUUUC | CUGACGCUGA | AGCACGAAAG | CUGGGGAGC AAACAGGAUU AGAUACCCUG GUAGUCCCAG |
| T26 | GGCAGUGUCC | UGGGUGGUAC | CUGACGCUGA | GAGGCGAAAG | CUAGGGGAGC GAACGGGAUU AGAUACCCCG GUAGUCCUAG |
| T12 | GGCAGUGUCC | UGGGUGGUAC | CUGACGCUGA | GAGGCGAAAG | CUAGGGGAGC GAACGGGAUU AGAUACCCCG GUAGUCCUAG |
| T81 | GGCAGUGUCC | UGGGUGGUAC | CUGACGCUGA | GAGGCGAAAG | CUAGGGGAGC GAACGGGAUU AGAUACCCCG GUAGUCCUAG |

*FIG. 2 (CONT.)*

| | | | | | | |
|---|---|---|---|---|---|---|
| AM180156 Ktedonobacter racemifer | CCGUAAACGA | UGACCACUAG | GUGUG-GGAG | -GUAUCGACC | CC-UUCCGUG | CCGUCCCAAA CGCAGUAAGU GGUCCGCCUG |
| AATI01000064 Herpetosiphon aurantiacus | CAGUAAACGA | UGCAUACCAG | GUGUGGGAUG | -GCGUUCGCG | UCGUUCCGUG | CCGCACUUUA CGCGAUGAGU AUGCCGCCUG |
| AAUI01000024 Chloroflexus aggregans | CCGUAAACGA | UGCCGGCUCG | GCGUUUGGCG | CGCGUGAGCG | U-GCUGGGUG | CCUUAGCUAA CGCGGUAAGC CGGCCGCCUG |
| AAUM01000026 Roseiflexus castenholzii | CCGUAAACGA | UGACCACUCG | GCGUGUGGCG | ACUAUUGACG | UCGCGGCGCG | CCUAAGCUUA CGGGUGAAGU GGUCCGCCUG |
| AJ420142 Sphaerobacter thermophilus | CAGUAAACGC | UGUGGACUAG | GUGUG-GGAG | -GUCUDGACC | CC-UUCCGUG | CCGGCGCUAA CGCAGUAAGU CCACCGCCUG |
| AJ431247 Dehalococcoides sp. BHI80-52 | CUGUAAACGA | UGUGAACUAG | GUGU-UCGCG | -CUGUU-AUG | GC-GUCAGUG | CCGGAGCUAA CGCGUUAAGU UCACCGCCUG |
| AY673403 Chloroflexi bacterium Ellin7237 | CCCUAAACGA | UGUCCACCGG | GUGC-CGGGG | -GUAUCGACC | CC-CUCGGUG | CCGAAGCUAA CCUGAUCAGU GGACCGCCUG |
| T26 | CCGUAAACGC | UGACCACUAG | GUGUGUGGGG | -AGAUCGACC | CC-CUGCGCG | CCGAAGCGAA GGCAUGAAGU GGUCCGCCUG |
| T12 | CCGUAAACGC | UGACCACUAG | GUGUGUGGGG | -AGAUCGACC | CC-CUGCGCG | CCGAAGCGAA CCCAUGAAGU GGUCCGCCUG |
| T81 | CCGUAAACGC | UGACCACUAG | GUGUGUGGGG | -AGAUCGACC | CC-CUGCGCG | CCGAAGCGAA CCGAUGAAGU GGUCCGCCUG |
| | | | | | | |
| AM180156 Ktedonobacter racemifer | GGGAGUACGG | UCGCAAGAUU | AAAACUCAAA | GGAAUUGACG | GGGACCCGCA | CAAGCAGCGG AGCGUGUGGU UUAAUUCGAU |
| AATI01000064 Herpetosiphon aurantiacus | GGGACUACGA | GCGCAAGCUU | AAAACUCAAA | GGAAUUGACG | GGGGCCCGCA | CAAGCAGCGG AGCGUGUGGU UUAAUUCGAC |
| AAUI01000024 Chloroflexus aggregans | GGGACUACGA | GCGCAAGCUU | AAAACUCAAA | GGAAUUGACG | GGGGCCCGCA | CAAGCAGCGG AGCGUGUGGU UUAAUUCGAC |
| AAUM01000026 Roseiflexus castenholzii | GGACUACGA | GCGCAAGCUU | AAAACUCAAA | GGAAUUGACG | GGGGCCCCCA | CAAGCAGCGG AGCGUGUGGU UUAAUUCGAG |
| AJ420142 Sphaerobacter thermophilus | GGGAGUACGG | CCGCAAGGCU | AAAACUCAAA | GGAAUUGACG | GGGGCCCCCA | CAAGCAGCGG AGCGUGUGGU UUAAUUCGAC |
| AJ431247 Dehalococcoides sp. BH-80-52 | GGGACUACGG | CCGCAAGGCU | AAAACUCAAA | GGAAUUGACG | GGGGCCCGCA | CAAGCAGCGG AGCGUGUGGU UUAAUUCGAU |
| AY673403 Chloroflexi bacterium Ellin7237 | GGGAGUACGG | CCGCAAGGUU | GAAACUCAAA | GGAAUUGACG | GGGGCCCGCA | CAAGCAGCGG AGCGUGUGGU UUAAUUCGAU |
| T26 | GGGAGUACGG | CCGCAAGGCU | AAAAACUCAAA | GGAAUUGACG | GGACCCCCA | CAAGCAGCGG AGCGUGUGGU UUAAUUCGAU |
| T12 | GGGAGUACGG | CCGCAAGGCU | AAAACUCAAA | GGAAUUGACG | GGGACCCCCA | CAAGCAGCGG AGCGUGUGGU UUAAUUCGAU |
| T81 | GGGAGUACGG | CCGCAAGGCU | AAAACUCAAA | GGAAUUGACG | GGGACCCCCA | CAAGCAGCGG AGCGUGUGGU UUAAUUCGAU |

*FIG. 2 (CONT.)*

| | | | | | | |
|---|---|---|---|---|---|---|
| AM180156 Ktedonobacter racemifer | GCAACGCGAA | GAACCUUACC | AAGUCUUGAC | AUGCA-GAUG | CACCAGCGGU | AAUGCGCUGU CC----CUUCG GGGCGUUUGC |
| AATI01000064 Herpetosiphon aurantiacus | GCAACGCGAA | GAACCUUACC | UAGUCUUGAC | AUAGCACUGC | AAGCUUCGGA | AAUGAAGUCG CC-----UUCG AGGGUGUGCU |
| AAUI01000024 Chloroflexus aggregans | GCAACCCGAA | GAACCUUACC | UGGGCUUGAC | AUGACGCUGC | AGCGCGGGGA | AACCGCGCGG CC-----UUUG AGGGUGCCUC |
| AAUM01000026 Roseiflexus castenholzii | GCAACCCGAA | GAACCUUACC | CAGGCUGGAC | AUGACGGUGC | AGCGGCGGGA | AACGUCCCGG CC-----UUCG AGGGACCGUC |
| AJ420142 Sphaerobacter thermophilus | GCAACGCGCA | GAACCUUACC | AGGGCUUGAC | AUCCCCCGAA | CCCCUGGGAA | ACCGGGGGUG CC-CUUCGGG GAGCCGGGAG |
| AJ431247 Dehalococcoides sp. BHI80-52 | GCAACGCGAA | GAGCCUUACC | UGGGUUUGAC | AUGUACGUAG | UAGGAA-GCC | GAAAGGCGAC CCACCCCUCG GGGAGCGUAC |
| AY673403 Chloroflexi bacterium Ellin7237 | GCGACGCGAA | GAACCUUACC | UGGGCUUGAC | AUGUG-AUUG | CACCAGGGGU | AAUGCCCUGU CCUCGCAAGA GAGCGGUCAC |
| T26 | GCAACGCGAA | GAACCUUACC | AGGGUUGGAC | AUGCACGCUG | AGGGUCCAGA | GAUGGGCGCG CC-CGCAAGG GAGCGCGU-GC |
| T12 | GCAACGCGAA | GAACCUUACC | AGGGUUGGAC | AUGCACGCUG | AGGGUCCAGA | GAUGGGCCGG CC-CGCAAGG GAGGCGU-GC |
| T81 | GCAACGCGAA | GAACCUUACC | AGGGUUGGAC | AUGCGCGCUG | AGGGUCCAGA | GAUGGGCCGG CC-CGCAAGG GAGCGC-GC |
| | | | | | | |
| AM180156 Ktedonobacter racemifer | ACAGGUGCUG | CAUGGCUGCUC | GUCAGCUCGU | GUCGUGAGAU | GUUGGGUUAA | GUCCCGCAAC GAGCGCAACC CCUACUGCCU |
| AATI01000064 Herpetosiphon aurantiacus | ACAGGUGCUG | CAUGGCUGUC | GUCAGCUCGU | GUCGUGAGAU | GUUGGGUUAA | GUCCCGCAAC GAGCGCAACC CCUGUGAGGU |
| AAUI01000024 Chloroflexus aggregans | ACAGGUGCUG | CAUGGCUGUC | GUCAGCUCGU | GUCGUGAGAU | GUUGGGUUAA | GUCCCGCAAC GAGCGCAACC CGCGUCGGUA |
| AAUM01000026 Roseiflexus castenholzii | ACAGGUGCUG | CAUGGCUGUC | GUCAGCUCGU | GUCGUGAGAU | GUUGGGUUCA | GUCCCGCAAC GAGCGCAACC CCUGCGGUUA |
| AJ420142 Sphaerobacter thermophilus | ACAGGUGCUG | CAUGGCUGUC | GUCAGCUCGU | GUCGUGAGAU | GUUGGGUUAA | GUCCCGCAAC GAGCGCAACC CCUGCGGUUA |
| AJ431247 Dehalococcoides sp. BHI80-52 | ACAGGUGCUG | CAUGGCUGUC | GUCAGCUCGU | GUCGUGAGAU | GUUGGGUUAA | GUCCCGCAAC GAGCGCAACC CUCGUGCUA |
| AY673403 Chloroflexi bacterium Ellin7237 | ACAGGUGCUG | CAUGGCUGUC | GUCAGCUCGU | GCCGUGAGGU | GUUGGGUUAA | GUCCCGCAAC GAGCGCAACC CCUGUGCUA |
| T26 | ACAGGUGCUG | CAUGGCUGUC | GUCAGCUCGU | GCCGUGAGGU | GUUGGGUUAA | GUCCCGCAAC GAGCGCAACC CCUGGGUCC |
| T12 | ACAGGUGCUG | CAUGGCUGUC | GUCAGCUCGU | GCCGUGAGGU | GUUGGGUUAA | GUCCCGCAAC GAGCGCAACC CUCGCUCCG |
| T81 | ACAGGUGCUG | CAUGGCUGUC | GUCAGCUCGU | GCCGUGAGGU | GUUGGGUUAA | GUCCCGCAAC GAGCGCAACC CUCGCUCCG |

*FIG. 2 (CONT.)*

```
AM180156 Ktedonobacter racemifer         AUUA----CA ACUUCUAGGC GCAACUGCC- CUCACG---- -GGAGGAAGG CGGGGAUGAC GUCAAGUCAG CACGGCCCUU
AATI01000064 Herpetosiphon aurantiacus   GUUA----CA AGUGUCACCU CAGACUGCCG UUGUCAACAA CGGAGGAAGG CGGGGAUGAC GUCAAGUCCG CAUGGCCCUU
AAUI01000024 Chloroflexus aggregans      GUUA----CC GGUGUCUACC GAGACUGCCG CCGAGACCGG CGGAGGAAGG CCCGGAUGAC GUCAAGUCAG CAUGGCCCUG
AAUM01000026 Roseiflexus castenholzii    GUUA----CC GGUGUCUAAC CGGACUGCCG UUCGG----- -GGAGGAAGG CGGGGAUGAC GUCAAGUCCG CAUGGCCCUG
AJ420142 Sphaerobacter thermophilus      GUUACG---GU GGUGUUUAGC CAGACUGCCG GGCACAACC- CGGAGGAAGG GGGGGAUGAC GUCAAGUCCG CAUGGCCCUG
AJ431247 Dehalococcoides sp. BHI80-52    GUUA----CA UGUGUCUAGC GAGACUGCCG GUUUACGC- CGGAGGAAGG AGGGGAUGAC GUCAAGUCAG CAUGGCCUUU
AY673403 Chloroflexi bacterium Ellin7237 GUUACCAUGG UGUGUCGGGC CCGACUGCCG CCCGGCAACG- CGGAGGAAGG CGGGGAUGAC GUCAAGUCAG CACGGCCCUG
T26                                      GUUG----GA AUUAUCCGAG GGGACUGCCG CCCACAACG- CGGAGGAAGG UGGGGAUGAC GUCAAGUCAG CAUGGCCCUG
T12                                      GUUG----GA GCUAUCCGAG GGGACUGCCG CCCACAACG- CGGAGGAAGG UGGGGAUGAC GUCAAGUCAG CAUGGCCCUG
T81                                      GUUG----GA UCUGUCCGAG GGCACUGCCG CGCACAACG- CGGAGGAAGG UGGGGAUGAC GUCAAGUCAG CAUGGCCCUG AM180156 Ktedonobacter racemifer         ACGACUUCGG CGACACACAC GCUACAAUGG CCAGUAACAA AGGGAUGCCA ACCCGCGAGG GGGAGCCAAG CUC-AAAAAC
AATI01000064 Herpetosiphon aurantiacus   ACGACUAGGG CGACACACAC GCUACAAUGG CUGGGA-GAA UGCGCCGCA CCUGGCAACA GGCAGCGAAU CGA--GAACA
AAUI01000024 Chloroflexus aggregans      ACGCCCGGGG CGACACACAC GCUACAAUGG CCACGA-CAA UGCGUGCCA CGCCGCAAGG CGGCGCUAAU CGC--CAAAC
AAUM01000026 Roseiflexus castenholzii    ACGCCUGGGG CGACACACAC GCUACAAUGG CGCCGA-CAA UGCGUGCGA CCGCCGAGC GAGGGAAAU CGC--CAAAC
AJ420142 Sphaerobacter thermophilus      ACGCCCUGGG CGACACACAC GCUACAAUGG CCGGGA-CAG CGGGCGGCCA AGCCGCAACG CGGAGCCAAU CCC-UCAAAC
AJ431247 Dehalococcoides sp. BHI80-52    AUGUCCAGGG CUACACACAC GCUACAAUGG CCGGUA-CAA CGGAGUAGCA AGUCCGCGAGA UGGAGCUAAU CCCAUCAAAG
AY673403 Chloroflexi bacterium Ellin7237 ACGUCCAGGG CGACACACAC GCUACAAUGG CCGAUA-CAA CGGGUCCGCA AGCCCGCGAGG CGGAGCCAAU CCCACCAAAG
T26                                      ACAUCCUGGG CGACACACAC GCUACAAUGG UCGGGA-CAG CGGGCAGCGA CCCGCAGCCAAU CCC-UUAAAC
T12                                      ACAUCCUGGG CGACACACAC GCUACAAUGG UCGGGA-CAG CGGGCAGCGA CCUGGCGACG GGGAGCCAAU CCC-UYAAAC
T81                                      ACAUCCUGGG CGACACACAC GCUACAAUGG UCGGGA-CAG CGGGCAGCGA CCCGCAGCGA CCCGCAGCGA GGAGCCAAU CCC-UCAAAC
```

*FIG. 2 (CONT.)*

```
AM180156 Ktedonobacter racemifer           CUGGUCUCAG UUCAGAUUGC AGGCUGAAAC UCCCCUGCAU GAAGCUGGAG UUGCUAGUAA CCGUAGGUCA GC-ACACUAC
AATI01000064 Herpetosiphon aurantiacus     CCAGUCACAG UUCAGAUUGG GGGCUGCAAC UCCCCCCCAU GAAGGCGGAG UUGCUAGUAA UCGCCGGUCA GCCAUACGGC
AAUI01000024 Chloroflexus aggregans        CUGGUCUCAG UGCAGAUCGG GGGCUGCAAC UCGCCCCCGU GAAGGCGGAG UUGCUAGUAA CCGGCUAUCA CCCAUGGCGC
AAUM01000026 Roseiflexus castenholzii      GGCGUCUCAG UGCAGAUCCG GGGCUGCAAC UCGCCCCCGU GAAGCGGAG UUGCUAGUAA CCGCGUAUCA GCCAUGGCGC
AJ420142 Sphaerobacter thermophilus        CCGGUCUCAG UUCGGAUUGG GGGCUGCAAC UCGCCCCCAU GAAGCGGAG UUGCUAGUAA CCGCAGGUCA GCCAUACUGC
AJ431247 Dehalococcoides sp. BHI80-52      CCGGUCUCAG UUCGGAUUGC AGGCUGCAAC UCGCCUGCAU GAAGUCGGAG UUGCUAGUAA CCCCUGUCA GCAAUAGCGC
AY673403 Chloroflexi bacterium Ellin7237   UCGGCCUCAG UUCCGAUUGU AGGCUGAAAC CCGGCCUGCGU GAAGCCGGAG UUCCUAGUAA CCGGGGUCA GC-ACACGC
T26                                        CCGAUCUCAG UGCAGAUUGC AGGCUGCAAC CCGCCUGCAU GAAGGAGGAG UUGCUAGUAA CCGCCGGUCA GC-ACACGGC
T12                                        CCCAUCUCAG UGCAGAUUGC AGGCUGCAAC CCGCCCUGCAU GAAGGAGGAG UUGCUAGUAA CCGCCGGUCA GC-ACACGGC
T81                                        CCGAUCUCAG UGCAGAUUGC AGGCUGCAAC CCGCCUGCAU GAAGGAGGAG UUGCUAGUAA CCGCCGGUCA GC-ACACGGC AM180156 Ktedonobacter racemifer           GGUGAAUACG UUCCCGGGUC UUGUACACAC CGCCCGUCAC ACCACGAAAG UCGGCAACAC CUGAAGCCGC CAGGCUAACU
AATI01000064 Herpetosiphon aurantiacus     GGUGAAUACG UACCCGGGCC UUGUACACAC CGCCCGUCAC CGCCCGUCAC UGGGAAACAC CUGAAGUCCG UGGGCUAACC
AAUI01000024 Chloroflexus aggregans        GGUGAAUACG UUCCCGGGCC UUGUACACAC CGCCCGUCAC GCCCGUCAC UGGCUAAUGC UUGAAGUCCG UGUGCUAACC
AAUM01000026 Roseiflexus castenholzii      GGUGAAUACG UACCCGGGCC UUGUACACAC CGCCCGUCAC GCCCGUCAC UGGCUAAUGC CUGAAGUCCG UCGCGCUAACC
AJ420142 Sphaerobacter thermophilus        GGUGAAUAUG UUCCCGGGCC UUGUACACAC CGCCCGUCAC GCACGAAAG CCGGCAACAC UGAAGCCGG UGGGCCAACC
AJ431247 Dehalococcoides sp. BHI80-52      GGUGAAUACG UUCCCGGGCC UUGUACACAC CGCCCGUCAC GUCAUGGGAG CCGGUAACAC CUGAAGUCGG CUGGCCAACC
AY673403 Chloroflexi bacterium Ellin7237   GGUGAAUACG UUCCCGGGCC UUGUACACAC CGCCCGUCAC ACCACGAAAG CCGGGACAC CUGAAGCCGC UGGGCAAACU
T26                                        GGJGAAUACG UUCUCGGGUC UUGUACACAC CGCCCGUCAC ACCACGAAAG CCGGCAACAC CUGAAGCCGC UGGGCGAACC
T-2                                        GGUGAAUACG UUCUCGGGUC UUGUACACAC CGCCCGUCAC ACCACGAAAG CGGGCAACAC CUGAAGCCGC UGGGGGAACC
T81                                        GGUGAAUACG UUCUCGGGUC UUGUACACAC CGCCCGUCAC ACCACGAAAG CCGGCAACAC CUGAAGCCGC UGGGGGAACC
```

*FIG. 2 (CONT.)*

| | | | | |
|---|---|---|---|---|
| AM180156 Ktedonobacter racemifer | CUUCG--GAG AGGCAGGCGU CGAGGGUGGG GUUGGUG--- | ---------- ---------- ---------- | ---------- ---------- ---------- | ---------- ---------- ---------- |
| AATI01000064 Herpetosiphon aurantiacus | GCA----AGG AGGCAGCGGC CGAGGGUCGG GCUCGUAACU | GGGACGAAGU CGUAACAAGG | UAGCCGUACC GGAAGGUGUG |
| AAUI01000024 Chloroflexus aggregans | CCCCACGGGG AGGCAGCGGC CGAGGGCAGG AGCCGCGACU | GGGACGAAGU CGUAACAAGG | UAGCCGUACC GGAAGGUGCG |
| AAUM01000026 Roseiflexus castenholzii | GUC----AGG AGGCAGCGGC CCGAGGGCAGG GCCAGCGACU | GGGACGAAGU CGUAACAAGG | UAGCCGUACC GGAAGGUCCG |
| AJ420142 Sphaerobacter thermophilus | CGAUAC-GGG AGGCAGCCGU CGAAGGUGGG GCUGGUGAUU | GGGACGAGU CGUAACAAGG | UAGCCGUAGC GGAAGCUGGG |
| AJ431247 Dehalococcoides sp. BH180-52 | UGCAA--GGG AGGGGGCUGC CUAGGGUGGG ACUGGUAACU | GGGACGAAGU CGUAACAAGG | UAAC------ ---------- |
| AY673403 Chloroflexi bacterium Ellir7237 | CUUCG--GAG AGGCAGGCGU CGAGGGUGGA ADCGGUGAUU | GGGGUG---- ---------- | ---------- ---------- |
| T26 | CCUCG--UCG GAGGGGAGGC AGGC------ ---------- | ---------- ---------- | ---------- ---------- |
| T12 | CCUCG--UCG GAGGGGAGGC AGG------- ---------- | ---------- ---------- | ---------- ---------- |
| T81 | CCUCG--UGA GAGGGGAGGC AGGCGUCGA- ---------- | ---------- ---------- | ---------- ---------- |

| | | |
|---|---|---|
| AM180156 Ktedonobacter racemifer | ---------- ---------- | ---------- |
| AATI01000064 Herpetosiphon aurantiacus | GCUGGAUCAC CUCCU----- ---------- | ---------- |
| AAUI01000024 Chloroflexus aggregans | GCUGGAUCAC CUCCUUU--- ---------- | ---------- |
| AAUM01000026 Roseiflexus castenholzii | GCUGGAUCAC CUCCUUU--- ---------- | ---------- |
| AJ420142 Sphaerobacter thermophilus | GCUGGUGAUU GGGACGAAGU CGUAACAAGG UAGCCGUAGC | GGAAGCU |
| AJ431247 Dehalococcoides sp. BH180-52 | ---------- ---------- | ---------- |
| AY673403 Chloroflexi bacterium Ellin7237 | ---------- ---------- | ---------- |
| T26 | ---------- ---------- | ---------- |
| T12 | ---------- ---------- | ---------- |
| T81 | ---------- ---------- | ---------- |

*FIG. 2 (CONT.)*

| | *Chloroflexus*-like isolate, T81, AM749782 | *Chloroflexus*-like isolate, T104, AM749781 | *Chloroflexus*-like isolate, P352, AM749769 | geothermal soil clone, AM749737 | *Chloroflexus*-like isolate, P359, AM749770 | *Chloroflexus*-like isolate, T12 | *Chloroflexus*-like isolate, T26 | *Chloroflexus*-like isolate, P353 | geothermal soil clone, Wku5-175 | geothermal soil clone, Wkt11-179 | *Chloroflexus*-like isolate, T24 |
|---|---|---|---|---|---|---|---|---|---|---|---|
| *Chloroflexus*-like isolate, T81, AM749782 | - | | | | | | | | | | |
| *Chloroflexus*-like isolate, T104, AM749781 | 98.7 | - | | | | | | | | | |
| *Chloroflexus*-like isolate, P352, AM749769 | 98.9 | 99.4 | - | | | | | | | | |
| geothermal soil clone, AM749737 | 98.6 | 99.4 | 99.5 | - | | | | | | | |
| *Chloroflexus*-like isolate, P359, AM749770 | 96.5 | 96.6 | 96.6 | 96.6 | - | | | | | | |
| *Chloroflexus*-like isolate, T12 | 98.3 | 99.1 | 98.9 | 98.9 | 96.5 | - | | | | | |
| *Chloroflexus*-like isolate, T26 | 98.7 | 99.7 | 99.4 | 99.4 | 96.6 | 99.2 | - | | | | |
| *Chloroflexus*-like isolate, P353 | 98.8 | 99.4 | 99.7 | 99.5 | 96.7 | 99.0 | 99.4 | - | | | |
| geothermal soil clone, Wku5-175 | 98.5 | 99.3 | 99.2 | 99.1 | 96.3 | 98.6 | 99.1 | 99.2 | - | | |
| geothermal soil clone, Wkt11-179 | 98.2 | 99.2 | 99.6 | 99.4 | 96.4 | 98.7 | 99.2 | 99.4 | 98.8 | - | |
| *Chloroflexus*-like isolate, T24 | 98.6 | 99.9 | 99.4 | 99.4 | 96.5 | 99.1 | 99.1 | 99.3 | 99.2 | 99.2 | - |

*FIG. 7*

| | grassland soil clone, EU044277 | uranium waste clone, AJ536887 | Chloroflexus-like isolate, T81, AM749782 | Kteodonobacter racemifer, AM180156 | Ktedonobacteria sp., SOSP1-0, AM180153 | Chloroflexus-like isolate, P359, AM749770 | c-horizon soil clone, EU335405 | Chloroflexus-like isolate, T12 | Chloroflexus-like isolate, T26 | geothermal soil clone Nga-67 |
|---|---|---|---|---|---|---|---|---|---|---|
| grassland soil clone, EU044277 | - | | | | | | | | | |
| uranium waste clone, AJ536887 | 81.1 | - | | | | | | | | |
| Chloroflexus-like isolate, T81, AM749782 | 82.6 | 78.9 | - | | | | | | | |
| Ktedonobacter racemifer, AM180156 | 86.9 | 80.6 | 79.7 | - | | | | | | |
| Ktedonobacteria sp., SOSP1-0, AM180153 | 88.0 | 81.1 | 80.3 | 97.7 | - | | | | | |
| Chloroflexus-like isolate, P359, AM749770 | 83.1 | 78.4 | 96.5 | 80 | 80.6 | - | | | | |
| c-horizon soil clone, EU335405 | 86.3 | 81.0 | 82.9 | 85.2 | 85.5 | 82.4 | - | | | |
| Chloroflexus-like isolate, T12 | 82.6 | 78.8 | 98.3 | 80 | 80.7 | 96.4 | 83.1 | - | | |
| Chloroflexus-like isolate, T26 | 82.9 | 79 | 98.7 | 80.4 | 81 | 96.5 | 83.2 | 99.1 | - | |
| geothermal soil clone Nga-67 | 78.9 | 83.7 | 77.6 | 78 | 79 | 78.8 | 76.6 | 77.9 | 77.8 | - |

*FIG. 8*

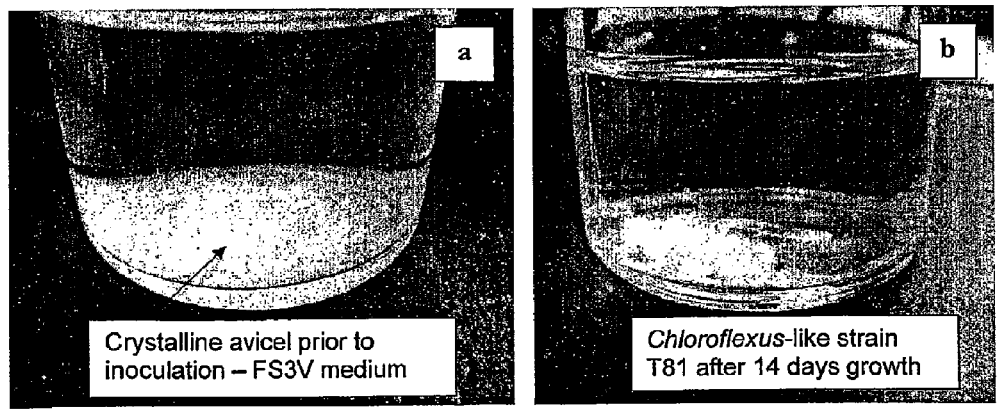

*FIG. 10*

CLASS OF *CHLOROFLEXI*-LIKE THERMOPHILIC CELLULOSE DEGRADING BACTERIA

RELATED APPLICATIONS

This application is a nationalization under 35 U.S.C. 371 of PCT/NZ2009/000034, filed Mar. 11, 2009 and published as WO 2009/113882 A1, on Sep. 17, 2009, which claimed priority under 35 U.S.C. 119(e) to U.S. Patent Application Ser. No. 61/035,414, filed Mar. 11, 2008; which applications and publication are incorporated herein by reference in their entirety.

FIELD OF THE INVENTION

This invention relates to a novel class of thermophilic cellulose degrading bacteria, specific strains from within the class, compositions containing same, and use of the strains as cellulose degrading agents. The invention has applications in the generation of ethanol from cellulose containing biomass such as forestry and plantation pulp and/or waste organic material.

BACKGROUND

It is now widely accepted that the current and predicted global warming is primarily due to anthropogenic 'greenhouse' emissions. The development of biologically-derived and environmentally sustainable fuel such as bioethanol is recognised as an important means for reducing our reliance on fossil fuels. At present, bioethanol derived from the microbial-mediated conversion of cellulose and hemicellulose—the world's most abundant biological materials—has environmental, and anticipated economic viability.

The current approach to converting biomass to ethanol involves essentially a three step process; (1) a pre-treatment process (including acid explosion) to allow access of cellulolytic enzymes to cellulose, lignin and hemicellulose polymers, (2) enzymatic degradation of polysaccharides to sugars, and (3) the anaerobic fermentation of sugars to ethanol. Step 2, cellulose hydrolysis, is the most expensive and difficult to carry out efficiently as the often crystalline structure of cellulose requires a multi-enzyme attack to hydrolyse glycosyl residues to sugars.

One of the major components in organic waste is cellulose. Degrading cellulose can also reduce the volume of organic waste that needs to be disposed of, as well as generating useful by-products such as ethanol.

Typically, the microbial cultures used to degrade cellulose, are mesophilic with optimal operating temperatures between 25 to 45° C. There is clear evidence indicating that cellulose degradation occurs rapidly at elevated temperatures. However, to date there are only limited numbers of thermophilic cellulose degrading microorganisms and only two aerobic cellulose-degrading thermophiles. Aerobic cellulose-degrading bacteria generate substantial quantities of cellulose degrading enzymes and have high cell yields (Lynd et al., (2002) *Microbial Mol Revs*, 66(3): 506-577), yet only two thermophilic aerobes, *Rhodothermus marinus* (Halldörsdóttir et al. (1998) *Appl Microbial and Biotech*, 49(3): 277-284) and *Caldibacillus cellulovorans* (Bergquist et al. (1999) *FEMS Microbial Ecol*, 28(2): 99-110) are currently described. *Rhodothermus marinus* grows optimally at 75° C., but only has a narrow range of cellulose substrates, and notably, does not degrade crystalline cellulose (Avicel®), a highly recalcitrant cellulose. *Caldibacillus cellulovorans* grows optimally at 68° C. and has a wider substrate utility including Avicel®, but prefers amorphous cellulose.

There is one other reported case of an aerobic cellulolytic and thermophilic bacteria, *Acidothermus cellulolyticus* (Mohagheghi et al., (1986) Int. J. System. Bacteriol. 36(3):435-443). However, *A. cellulyticaus* has a temperature optimal of only 50-55° C. and temperature range of only 37-65° C.

A need therefore still exists for thermophilic bacteria capable of degrading cellulose, including at high temperatures. Accordingly, it is an object of this invention to provide an aerobic thermophilic bacteria capable of cellulose degradation, or to at least provide the public with a useful choice.

SUMMARY OF THE INVENTION

In a first aspect, the invention provides a biologically pure culture of Chloroflexi-like microorganism designated T81 on deposit at Deutsche Sammlung von Mikroorganismen und Zellkulturen GmbH, Mascheroder Weg 1b, D-38124, Braunschweig, Germany, Accession No. DSM 21103 (deposited 30 Jan. 2008), or a culture having the identifying characteristics thereof.

The invention also provides a biologically pure culture of a Chloroflexi-like microorganism designated T26 on deposit at Deutsche Sammlung von Mikroorganismen und Zellkulturen GmbH, Mascheroder Weg 1b, D-38124, Braunschweig, Germany, Accession No. DSM 21252 (deposited 6 Mar. 2008), or a culture having the identifying characteristics thereof.

The invention also provides a biologically pure culture of a Chloroflexi-like microorganism designated T12 on deposit at Deutsche Sammlung von Mikroorganismen und Zellkulturen GmbH, Mascheroder Weg 1b, D-38124, Braunschweig, Germany, Accession No. DSM 21251 (deposited 6 Mar. 2008), or a culture having the identifying characteristics thereof.

In another aspect, the invention provides a biologically pure culture of a thermophilic Chloroflexi-like bacteria designated T81 which is capable of degrading cellulose and has the following identifying characteristics:

Gram positive, filamentous bacteria with branching hyphae and cells of 0.2 to 0.4 μm in width and 30 μm or greater in length, has white vegetative mycelia with yellow under-layer aerobe, pH growth range 3.1-7.5, at temperatures between 40° C.-75° C., growth on starch, carboxymethylcellulose, xylan, pullulan, Avicel® (crystalline cellulose), mannose, trehalose, cellulosic pulp, and cellobiose as the sole energy source on FS3V medium.

The invention also provides a biologically pure culture of a thermophilic Chloroflexi-like bacteria designated T26 which is capable of degrading cellulose and has the following identifying characteristics:

Gram positive, filamentous bacteria with branching hyphae and cells of 0.2 to 0.4 μm in width and 30 μm or greater in length, has white vegetative mycelia with yellow under-layer aerobe, pH growth range 3.1-7.5, at temperatures between 40° C.-75° C., growth on starch, carboxymethylcellulose, xylan, pulluan, Avicel® (crystalline cellulose), mannose, trehalose, cellulosic pulp, and cellobiose as the sole energy source on FS3V medium.

The invention also provides a biologically pure culture of a thermophilic Chloroflexi-like bacteria designated T12 which is capable of degrading cellulose and has the following identifying characteristics:

Gram positive, filamentous bacteria with branching hyphae and cells of 0.2 to 0.4 μm in width and 30 μm or greater in length, has white vegetative mycelia with yellow under-layer aerobe, pH growth range 3.1-7.5, at temperatures between 40° C.-75° C., growth on starch, carboxymethylcellulose, xylan, pullulan, Avicel® (crystalline cellulose), mannose, trehalose, cellulosic pulp, and cellobiose as the sole energy source on FS3V medium.

In a further aspect, the invention provides a biologically pure culture of a cellulose degrading thermophilic Chloroflexi-like microorganism comprising a 16S ribosomal subunit nucleic acid sequence selected from the group consisting of:
(a) SEQ ID NO:1 or a variant or fragment thereof;
(b) SEQ ID NO:2 or a variant or fragment thereof;
(c) SEQ ID NO:3 or a variant or fragment thereof;
(d) a variant nucleic acid sequence that has greater than 81% identity to a nucleic acid sequence of any one of (a) to (c);
(e) a nucleic acid sequence complementary to a nucleic acid of any one of (a) to (d); and
(f) a sequence of at least 10 nucleotides in length, capable of hybridising to the sequence of any one of (a) to (e) under stringent hybridisation conditions.

In a still further aspect, the invention provides an isolated cellulose degrading Chloroflexi-like microorganism comprising SEQ ID NO:1.

The invention also provides an isolated cellulose degrading Chloroflexi-like microorganism comprising SEQ ID NO:2.

The invention also provides an isolated cellulose degrading Chloroflexi-like microorganism comprising SEQ ID NO:3.

In a further aspect, the invention provides a cellulose degrading composition comprising at least one microorganism of the invention and a carrier or diluent.

In another aspect, the invention provides a method of degrading a cellulose containing material which method comprises treating the material with a composition of the invention, or one or more microorganisms of the invention effective to degrade cellulose.

Although the invention is broadly as described above, it will be appreciated by those persons skilled in the art that the invention is not limited thereto but also includes embodiments of which the following description gives examples.

BRIEF DESCRIPTION OF THE FIGURES

FIG. 2 shows the alignment of 16S rRNA gene sequences of the bacterial strain T81, T26 and T12 and other closely related Chloroflexi and Chloroflexi-like species (SEQ ID NOs: 4-13).

FIG. 7 16S rRNA gene sequence similarity of thermophilic *Chloroflexus*-like strains. Strains T81, T12 and T26 are highlighted in bold. The greatest sequence dissimilarities between isolates are highlighted by the bold square.

FIG. 8 16S rRNA gene sequence similarity of thermophilic *Chloroflexus*-like strains and most closely related strains from the phylum Chloroflexi. Strains T81, T12 and T26 are highlighted in bold. The closest sequence similarities between thermophilic *Chloroflexus*-like isolates and other members of the phylum Chloroflexi are highlighted by the bold square.

FIG. 10 photographs showing avicel cultures prior to inoculation (a) and after 14 days of incubation with Chloroflexi-like strain T81 (b).

DEFINITIONS

Figure 1:
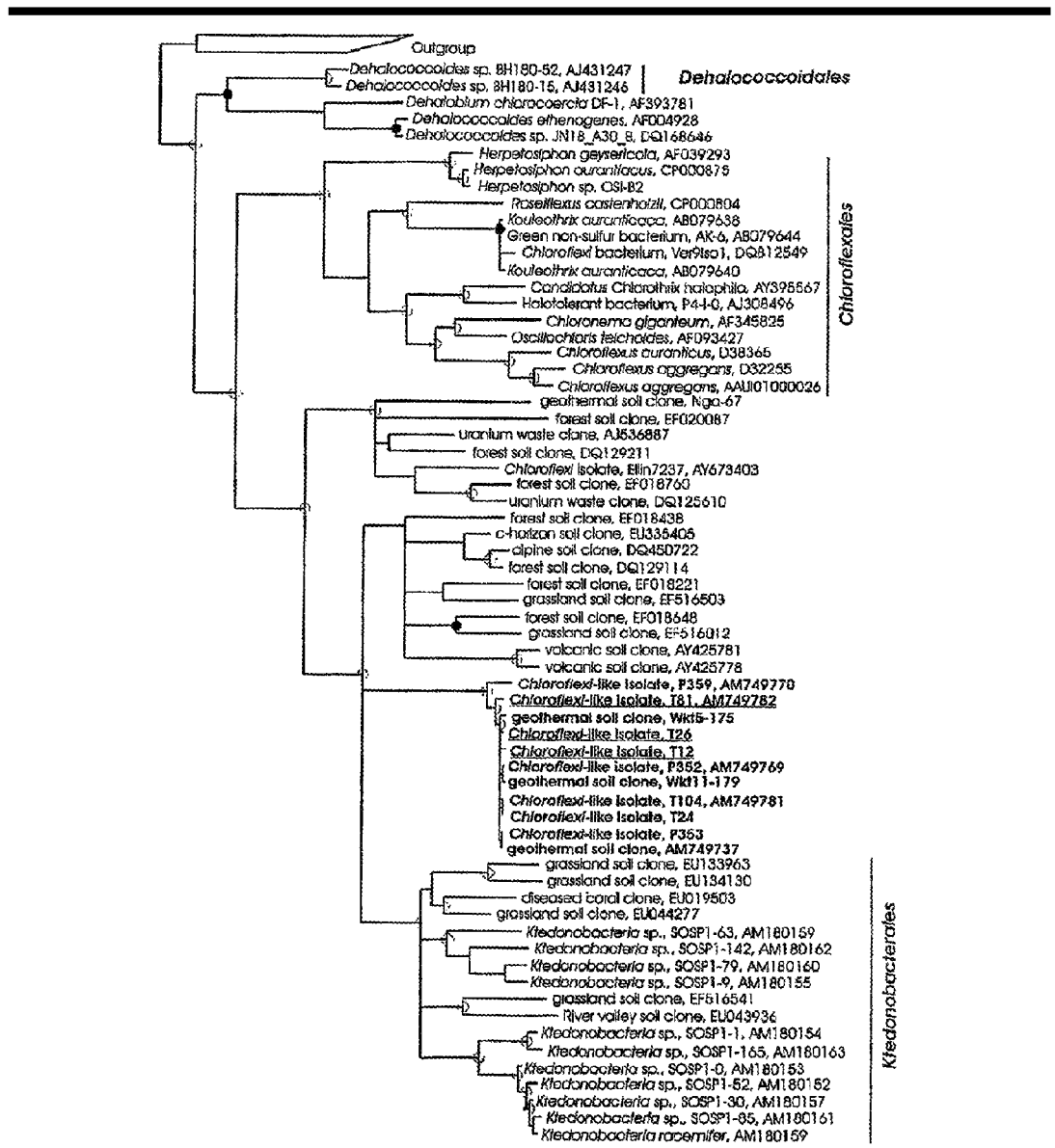
FIG. 1 is a maximum-likelihood quartet-puzzling phylogenetic tree showing the position of cultivated isolates and environmental 16S rRNA clones belonging to the phylum Chloroflexi. Described orders within the Chloroflexi are marked. The tree was rooted against a group of seven sequences from other phyla. Quartet-puzzling support values (10,000 resamples) are represented by the following symbols: ○≥90%; ●≥80%; ◇≥70% at each internal branch. Multifurcations are drawn where the support values for a bifurcation values is <50%. The bar indicates 0.1 changes per nucleotide position.

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

The term "polynucleotide(s)," as used herein, means a single or double-stranded deoxyribonucleotide or ribonucleotide polymer of any length, and include as non-limiting examples, coding and non-coding sequences of a gene, sense and antisense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, fragments, genetic constructs, vectors and modified polynucleotides. Reference to a nucleic acid molecule is to be similarly understood.

A "fragment" of a polynucleotide sequence provided herein is a subsequence of contiguous nucleotides that is capable of specific hybridization to a target of interest, e.g., a sequence that is at least 10 nucleotides in length. The fragments of the invention comprise at least 10, 15 nucleotides, 20, 25, 30, 50, 100, 200, 300, 400, 500, 600, 700, 800, 900, 1000, 1100, 1200, 1300, 1325, 1350, 1375, 1383 or 1391 contiguous nucleotides of a polynucleotide of SEQ ID NOs:1, 2, or 3. A fragment of a polynucleotide sequence can be used as a primer, a probe, included in a microarray, or used in polynucleotide-based selection methods herein.

The term "FS3V medium" as used herein refers to a medium of the following formula (per L): 0.4 g $NH_4Cl$; 0.1 g $KH_2PO_4$; 0.04 g $MgSO_4.7H_2O$; 0.02 g $CaCl_2.6H_2O$; 6 ml FeEDTA solution (see below), 6 ml of trace elements 1 solution (see below) and 2 ml of trace elements 2 solution (see below). The medium was adjusted to a pH of 4.5 using dilute HCl. One hundred mg $L^{-1}$ of a vitamin mixture (see below) and 100 mg $L^{-1}$ yeast extract was also added through a 0.2 μm filter after autoclaving to this medium.

The FeEDTA solution contained (per L): 1.54 g FeSO$_4$.7H$_2$O; 2.06 g Na$_2$EDTA. Trace elements solution 1 contained (per L): 0.44 g ZnSO$_4$.7H$_2$O; 0.20 g CuSO$_4$.5H$_2$O; 0.19 g MnCl.4H$_2$O; 0.06 g Na$_2$MoO$_4$.2H$_2$O; 0.10 g H$_3$B0$_3$; 0.08 g CoCl$_2$.6H$_2$O. Trace elements solution 2 contained (per L): 1.5 g nitrilotriacetic acid; 0.2 g Fe(NH$_4$)$_2$(SO$_4$)$_2$.6H$_2$O; 0.2 g Na$_2$SeO$_3$ 0.1 g CoCl$_2$.6H$_2$O; 0.1 g MnSO$_4$.2H$_2$O; 0.1 g Na$_2$MoO$_4$.2H$_2$O; 0.1 g Na$_2$WO$_4$.2H$_2$O; 0.1 g ZnSO$_4$.7H$_2$O; 0.04 g AlCl$_2$.6H$_2$O; 0.025 g NiCl$_2$.6H$_2$O; 0.01 g H$_3$BO$_3$ 0.01 g CuSO$_4$.5H$_2$O (pH 7). The vitamin mixture contained (in 100 mg): 0.8 mg folic acid; 8 mg vitamin B1; 4 mg vitamin B2; 1 mg niacin; 10 mg niacinamide; 15 mg pantothenate; 15 mg pyridoxine; 5 mg cobalamin; 5 mg biotin; 15 mg choline; 15 mg inositol; 7 mg para-amino benzoic acid.

The term "AOM1 medium" as used herein refers to a medium of the following formula (per L): 4 g NH$_4$SO$_4$; 0.25 g NaHCO$_3$ 0.05 g KH$_2$PO$_4$; 0.666 g MgSO$_4$.7H$_2$O; 5 mg CaCl$_2$.6H$_2$O; 10 mg yeast extract, 10 mg vitamins, 1 ml FeEDTA solution (see above) The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

The term "isolated" as applied to a microorganism describes a microorganism that has been obtained or removed from its natural environment and it subsequently maintained in a laboratory environment as known in the art.

The term "biologically pure culture" as used herein refers in one embodiment to at least 90%, or 95%, 96%, 97%, 98%, or 99%, or 100% homogeneity of a microorganism in a sample.

The term "isolated" as applied to the polynucleotide sequences disclosed herein is used to refer to sequences that are removed from their natural cellular environment. An isolated molecule may be obtained by any method or combination of methods including biochemical, recombinant, and synthetic techniques. The polynucleotide sequences may be prepared by at least one purification step.

The term "recombinant" refers to a polynucleotide sequence that is removed from sequences that surround it in its natural context and/or is recombined with sequences that are not present in its natural context.

As used herein, the term "variant" refers to polynucleotide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the polynucleotides useful in the invention have biological activities or properties that are the same or similar to those of the parent polynucleotides. The term "variant" with reference to polynucleotides encompasses all forms of polynucleotides as defined herein.

Variant polynucleotide sequences preferably exhibit at least 82%, at least 83% at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to a sequence of the present invention. Identity is found over a comparison window of at least 10 nucleotide positions, at least 15 nucleotide positions, at least 20 nucleotide positions, at least 25 nucleotide positions, at least 40 nucleotide positions, at least 50 nucleotide positions, or over the entire length of a polynucleotide of the invention.

Polynucleotide sequence identity may be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http://www.hgmp.mrc.ac.uk/Software/EMBOSS/. The European Bioinformatics Institute server also provides the facility to perform EMBOSS-needle global alignments between two sequences on line at http://www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

In this case alignments were effected using the ARB phylogeny software (Ludwig et al. (2004) *Nucleic Acids Res*, 32: 1363-1371.) and the 2007 ARB-Silva database (release SILVA-89, http://www.arb-silva.de/).

Phylogenetic trees were constructed using the FastDNAml maximum likelihood algorithm in the ARB software environment. Phylogenetic trees were constructed using the TREE-PUZZLE, a quartet-puzzling maximum-likelihood algorithm in the ARB software environment. The tree was rooted against a group of seven sequences from other phyla, including *Synecoccus elongates* (D83715), *Arthrospira platensis* (DQ393280), *Alicyclobacillus acidocaldarius* (AB059663), *Geobacillus stearothermophilus*(AY608942), *Methylococcus capsulatus* (AE017282), *Methylosinus trichosporium* (AJ431385) and *Streptomyces halotolerans* (AY376166). Quartet-puzzling support values were generated using 10,000 resamples.

Polynucleotide variants also encompass those which exhibit a similarity to one or more of the specifically identified sequences that is likely to preserve the functional equivalence of those sequences and which could not reasonably be expected to have occurred by random chance. The GAP program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences exhibit an E value of less than $1\times10^{-5}$, less than $1\times10^{-6}$, less than $1\times10^{-9}$, less than $1\times10^{-12}$, less than $1\times10^{-15}$, less than $1\times10^{-18}$ or less than $1\times10^{-21}$ when compared with any one of the specifically identified sequences.

Polynucleotide sequence identity and similarity can also be determined in the following manner. The subject polynucleotide sequence is compared to a candidate polynucleotide sequence using sequence alignment algorithms and sequence similarity search tools such as in Genbank, EMBL, Swiss-PROT and other databases. Nucleic Acids Res 29:1-10 and 11-16, 2001 provides examples of online resources. BLASTN (from the BLAST suite of programs, version 2.2.13 March 2007 in bl2seq (Tatiana A. et al, FEMS Microbiol Lett.

174:247-250 (1999), Altschul et al., Nuc. Acids Res 25:3389-3402, (1997)), which is publicly available from NCBI (ftp://ftp.ncbi.nih.gov/blast/) or from NCB1 at Bethesda, Md., USA may be used. The default parameters of bl2seq are utilized except that filtering of low complexity parts should be turned off.

Where BLASTN is used in the determination of sequence identity for polynucleotide variants according to the present invention the identity of polynucleotide sequences may be examined using the following UNIX command line parameters:

bl2seq -i nucleotideseq1 -j nucleotideseq2 -F F -p blastn

The parameter -F F turns off filtering of low complexity sections. The parameter -p selects the appropriate algorithm for the pair of sequences. The bl2seq program reports sequence identity as both the number and percentage of identical nucleotides in a line "Identities=".

Alternatively, variant polynucleotides may be polynucleotides which hybridize to the specified polynucleotide sequence, or a complement thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing, incorporated herein by reference). Tm for polynucleotide molecules greater than about 100 bases can be calculated by the formula Tm=81.5+0.41% (G+C-log(Na+) (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for a polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

In one embodiment stringent conditions use 50% formamide, 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulphate at 42° C., with washes at 42° C. in 0.2×SSC and 50% formamide at 55° C., followed by a wash comprising of 0.1×SSC containing EDTA at 55° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

The term "treat", "treating" or "treatment" refers to the contacting of cellulose containing material with a composition of the invention or one or more microorganism(s) of the invention. In one embodiment, the compositions or microorganism(s) are used in an amount effective to degrade cellulose.

An "amount effective to degrade cellulose" means an amount of the microorganism(s), or a composition of the invention capable of effecting full (96%, 97%, 98%, 99%, or 100% degradation) or partial degradation of cellulose in a cellulose containing material.

"Partial degradation" means degradation of at least 10%, at least 20%, at least 30%, at least 40%, at least 50%, at least 60%, at least 70%, at least 80%, at least 90%, or at least 95% degradation of cellulose in a cellulose containing material.

It is intended that reference to a range of numbers disclosed herein (for example 1 to 10) also incorporates reference to all related numbers within that range (for example, 1, 1.1, 2, 3, 3.9, 4, 5, 6, 6.5, 7, 8, 9 and 10) and also any range of rational numbers within that range (for example 2 to 8, 1.5 to 5.5 and 3.1 to 4.7) and, therefore, all sub-ranges of all ranges expressly disclosed herein are expressly disclosed. These are only examples of what is specifically intended and all possible combinations of numerical values between the lowest value and the highest value enumerated are to be considered to be expressly stated in this application in a similar manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

DETAILED DESCRIPTION OF THE INVENTION

As noted above, the present invention is directed to thermophilic cellulose degrading Chloroflexi-like bacteria. More particularly, the applicants have identified and isolated for the first time aerobic, thermophilic chemoorganotrophic bacteria of a previously uncultured class of Chloroflexi.

In one aspect, the invention provides a biologically pure culture of the Chloroflexi-like microorganisms designated T81, T26 and T12 or a culture having the identifying characteristics of any one of these cultures.

Identifying characteristics include aerobic, thermophilic growth with a maximum growth temperature of about 75° C., growth in the range 40° C. to 75° C., and optimal growth temperature of between 50-65° C. Cells are Gram-positive, filamentous with branching hyphae and single cell filaments with dimensions of 0.2 to 0.4 µm in width and greater than 30 µm in length. Vegetative mycelia is white with yellow underlayer. Cells were frequently branched without septa, but occasional septa like cell divisions were observed connecting individual cells in filaments. Newly developing branches were usually characterised by an electron-dense region in the branching tip. The cells are moderate acidophiles with a pH optima of 4.5-6.0 and a pH range of between pH 3.1 and 7.5. Each Chloroflexi-like strain possessed differing abilities to utilise cellulosic substrates, simple sugars and alcohols as energy sources (Table 3). However, in general the cells were able to utilise most cellulosic substrates, in particular Avicel®, carboxymethyl cellulose (CMC), xylan, starch, pullulan, cellobiose, mannose, trehalose, and a selection of commercial cellulosic pulps and most sugars and alcohols tested.

The morphology was similar to the recently described proposed genus "*Ktedonobacter*" (Cavaletti et al. (2006) *Appl Environ Microbial*, 72: 4360-4369). The species *Ktedono-* bacter racemifer shares a number of similar traits to Chloroflexi. However, the Chloroflexi-like species of the invention differ from *K. racemifer* in its obligate thermophily and the broad range of energy sources capable of supporting growth including cellulosic substances, simple sugars and alcohols (see Table 3 and discussion below). *Ktedonobacter* species are the closest cultivated neighbours based on 16S rRNA phylogeny. The similarity was only ~81% to the type strain (FIG. 7 and Table 1).

Figure 9:
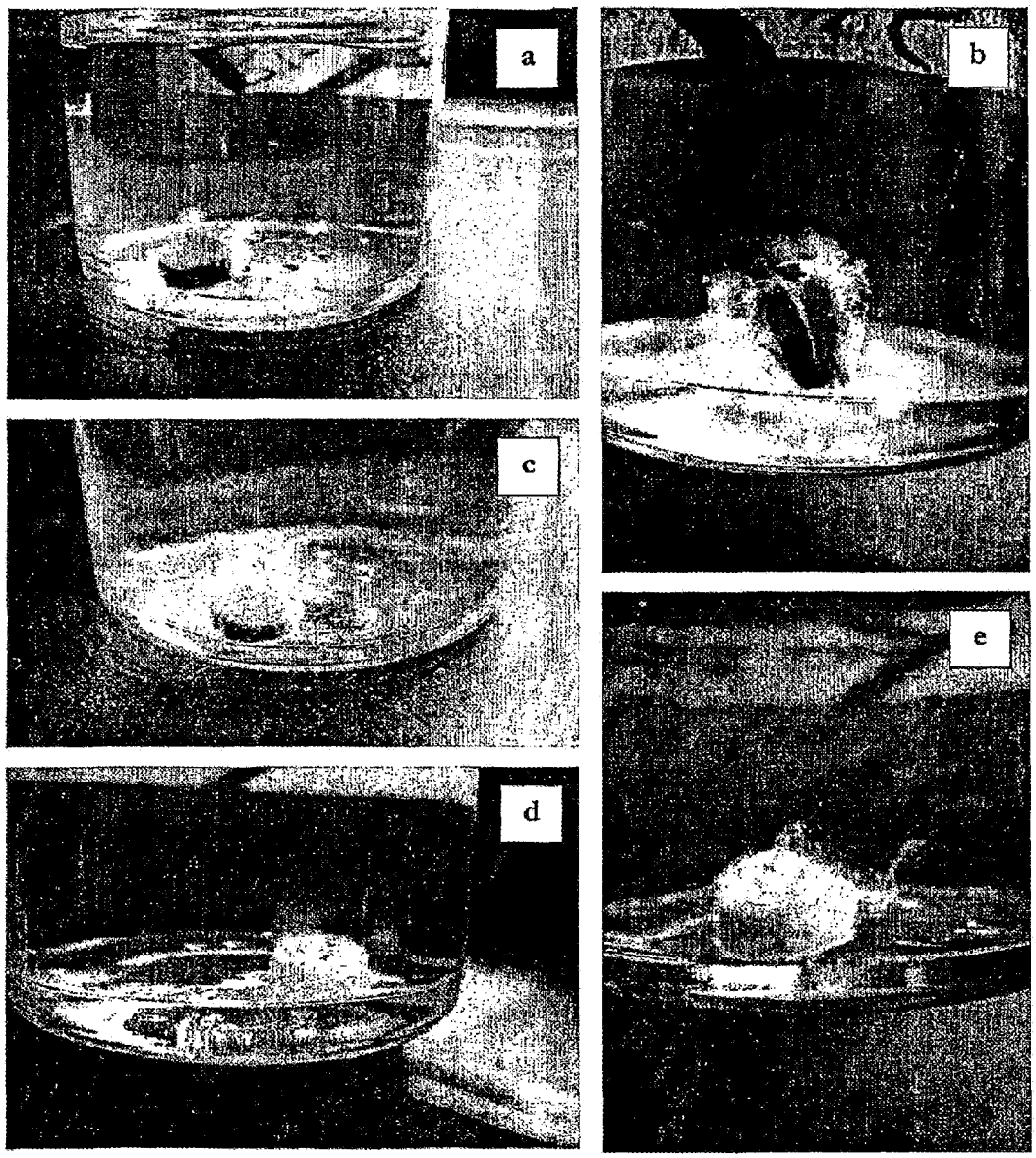
FIG. 9 photographs showing Chloroflexi-like strains attached to cellulosic pulp 'tablets'. Image (a); T81 with K20 pulp, (b) T26 with K20 pulp, (c) T81 with K20 pulp, (d) T26 with BKT pulp, and (e) T81 with E90 pulp. The cultures shown are all 4 days old. Descriptions of pulp types included in Example 3—Commercial pulps.

Colony morphology for the Chloroflexi-like microorganisms is white vegetative mycelia with yellow under-layer; pH growth range of 3.1 to 7.5; and at temperatures between 40° C.-75° C., when grown on solid medium. When grown on cellulosic-based sodifying medium such as gellan (Sigma, Missouri, USA, 91910) or phytagel (Sigma, P8169), the resultant colonies form pock marks or craters within the gel. Growth on gellan or phytagel occurred when the media contained no other energy source beside gellan or phytagel and mineral salts. In aqueous medium, the Chloroflexi-like microorganisms form small white mycelial tufts that associated with cellulosic substrates (FIGS. 8 and 9). Growth was supported on the following substrates in aqueous FS3V medium by all of the individual strains as described in Table 3: gellan, phytagel, agar, carboxymethylcellulose, xylan, pectin, xanthan, Avicel®, sodium alginate, starch, cellulose filter paper, dextrin, gellan, pullulan, D-glucose, D-fructose, D-galactose, D-mannose, D-arabinose, xylose, L-rhamnose monohydrate, D-N-actetylglucosamine, sucrose, D-maltose, D-celloniose, D-trehalose, yeast extract, sodium pyruvate, sodium citrate, sodium acetate, methanol, ethanol, 1-propanol, 2-propanol, pentanol and butanol, tryptic soy broth, Luria-Bertani broth, R2A, and nutrient broth.

Unique features of T12 were its ability to grow on dextrin as the sole energy source, inability to utilise sugars for growth at near neutral pH (pH 6.5) on AOM1 medium, and its ability to grow on ethanol concentrations up to and including 5.0% (v/v) at acid pH (pH 4.5) on FS3V medium.

T81 demonstrated the broadest ability to utilise sugars for growth at near neutral pH (pH 6.5), and under acid conditions (pH 4.5). Growth was on AOM1 and FS3V medium respectively.

T81 on both media grew using D-glucose, D-maltose, D-fructose, D-galactose, D-mannose, D-xylose, L-rhamnose monohydrate, D-cellobiose, D-trehalose, sucrose and raffinose. T81 also grew using D-arabinose and D-ribose at acid pH (pH 4.5) on FS3V medium.

T26 could not use dextrin as an energy source on either FS3V or AOM1 medium, and exhibited abilities to utilise sugars as energy sources which were intermediate to those demonstrated by T12 and T81. That is, T26 could use all the same sugars as T81 when grown on FS3V medium, but on AOM1 medium could grow only with D-glucose, L-rhamnose monohydrate, D-cellobiose, sucrose and D-N-actylglucosamine as sugar energy sources.

Growth on gellan or phytagel occurred when the media contained no other energy source beside gellan or a few mg $L^{-1}$ of yeast extract, vitamins, and mineral salts. Subsequent experiments have since demonstrated that the requirement for yeast extract and vitamins as growth factor supplements is not obligate.

Growth temperatures in the range 50° C. to 65° C. are preferred for growth. Temperatures of 60-65° C. are particularly suitable.

Preferably, the incubation vessel includes 5-10% $CO_2$ in the headspace of the vessel. It is currently believed that $CO_2$ enrichment facilitates growth of the bacteria of the invention conveniently referred to as Chloroflexi-like bacteria based on phylogenetic analysis to date. Subsequent experiments have since demonstrated that the requirement for $CO_2$ as a carbon-source is not obligate.

The Chloroflexi-like bacteria of the invention were isolated at 60° C. and pH's 5.5 and 6.5.

Bacterial strains T81, T26 and T12 were deposited with Deutsche Sammlung von Mikroorganismen and Zellkulturen GmbH, Mascheroder Weg 1b, D-38124, Braunschweig, Germany, on 30 Jan. 2008, 6 Mar. 2008, and 6 Mar. 2008, respectively, under the provisions of the Budapest Treaty for the International Recognition of the Deposit of Microorganisms for the Purposes of Patent Procedure and have been accorded DSM Accession Nos. DSM 21103, 21252 and 21251 respectively.

Molecular analysis of the 16S rRNA content of isolates of the invention was carried out using known art techniques set out in the examples. Sequence alignment and phylogenetic trees (FIGS. 1 and 2) were similarly developed using techniques well known to the skilled reader. The molecular analysis determined that the 16S rRNA sequences were unique compared to known bacteria, sharing at most 81% identity with known bacterial sequences.

Accordingly, in another aspect, the invention provides a biologically pure culture of a cellulose degrading thermophilic Chloroflexi-like microorganism comprising a 16S ribosomal subunit nucleic acid sequence selected from the group consisting of:

(a) SEQ ID NO:1 or a variant or fragment thereof;
(b) SEQ ID NO:2 or a variant or fragment thereof;
(c) SEQ ID NO:3 or a variant or fragment thereof;
(d) a variant nucleic acid sequence that has greater than 81% identity to a nucleic acid sequence of any one of (a) to (c);
(e) a nucleic acid sequence complementary to a nucleic acid of any one of (a) to (d); and
(f) a sequence of at least 10 nucleotides in length, capable of hybridising to the sequence of any one of (a) to (e) under stringent hybridisation conditions.

In one embodiment the variant nucleic acid sequence has at least 82%, 83%, 84%, 85%, 86%, 87%, 88%, 89%, 90%, 91%, 92%, 93%, 94%, 95%, 96%, 97%, 98%, or 99% identity to a nucleic acid sequence of any one of (a) to (c).

The polynucleotide can be isolated from a biological sample using a variety of techniques known to those or ordinary skill in the art. For example, using die FastDNA SPIN kit available from Q-BIOgene (MP Biomedicals, Ca, USA) according to manufacturers instructions. Also, such polynucleotides can be isolated through use of the polymerase chain reaction (PCR) described in Mullis et al. 1994, The Polymerase Chain Reaction, Birkhauser and U.S. Pat. No. 4,582,788. The polynucleotides can be amplified using primers, as described herein from the polynucleotide sequences of the invention. For example, according to the technique of Weisberg et al (1991). *J Bacteriol* 2: 697-703, or Mullis or Sambrook supra).

Further methods for isolating polynucleotides include use of all, or portions of, the polynucleotide of the invention, particularly a polynucleotide having a sequence set forth in SEQ ID NO:1, SEQ ID NO:2 or SEQ ID NO:3, as hybridization probes. The technique of hybridizing labeled polynucleotide probes to polynucleotides immobilized on solid supports such as nitrocellulose filters or nylon membranes, can be used to screen genomic or cDNA libraries. Similarly, probes may be coupled to beads and hybridized to the target sequence. Isolation can be effected using known art protocols such as magnetic separation. Exemplary stringent hybridization and wash conditions are as given above. (Sambrook et al., Supra)

Polynucleotide fragments may be produced by techniques well-known in the art such as restriction endonuclease digestion and oligonucleotide synthesis.

A partial polynucleotide sequence may be used as a probe, in methods well-known in the art to identify the corresponding full length polynucleotide sequence in a sample. Such methods include PCR-based methods, 5'RACE (Methods Enzymol. 218: 340-56 (1993); Sambrook et al., Supra) and hybridization-based method, computer/database-based methods. Detectable labels such as radioisotopes, fluorescent, chemiluminescent and bioluminescent labels may be used to facilitate detection. Inverse PCR also permits acquisition of unknown sequences, flanking the polynucleotide sequences disclosed herein, starting with primers based on a known region (Triglia et al., *Nucleic Acids Res* 16, 8186, (1998)). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Supra, Sequencher, Gene Codes Corporation, Michigan, USA). Primers and primer pairs which allow amplification of polynucleotides of the invention, also form a further aspect of this invention.

Variants (including orthologues) may be identified by the methods described. Variant polynucleotides may be identified using PCR-based methods (Mullis et at, Eds. 1994 The Polymerase Chain Reaction, Birkhauser). Typically, the polynucleotide sequence of a primer, useful to amplify variants of polynucleotide molecules by PCR, may be based on a sequence encoding a conserved region of the corresponding amino acid sequence.

Further methods for identifying variant polynucleotides include use of all, or portions of the specified polynucleotides as hybridization probes to screen genomic or cDNA libraries as described above. Hybridisation conditions may also be less stringent than those used when screening for sequences identical to the probe.

The variant sequences, may be identified by the computer-based methods discussed above.

Multiple sequence alignments of a group of related sequences can be carried out with CLUSTALW (Thompson, et al., Nucleic Acids Research, 22:4673-4680 (1994), http://www-igbmc.u-strasbg.fr/BioInfo/ClustalW/Top.html) or T-COFFEE (Cedric Notredame et al., (2000), *J Mol Biol* 302: 205-217) or PILEUP, which uses progressive, pairwise alignments. (Feng et at, (1987) *J Mol Evol* 25; 351).

Probes and primers as discussed above are also contemplated by the present invention. Typical primer lengths are 10 to 35 nucleotides, or 15 to 30 nucleotides but primers can be of any suitable length.

As also noted above, the invention contemplates variants and fragments of the nucleotide sequences of SEQ ID NOs: 1, 2 and 3. These variants and fragments include artificially produced sequences, alleleic variants, degenerate sequences, homologs and sequences with labels known in the art added.

Using the nucleotide sequences herein, the art skilled worker can obtain or identify similar sequences from other species, copy the sequences, or produce variants and fragments amongst other things.

The invention also provides a cellulose degrading composition comprising at least one microorganism of the invention and a diluent or carrier. The diluent or carrier is in one embodiment a delivery vehicle for the microorganism(s) of the invention. The carrier or diluent must be compatible with the viability of the bacteria. Suitable carriers and diluents are known in the art and include aqueous (e.g. water) or non-aqueous carriers. Examples of carriers are water, growth medium including FS3V and AOM1, agar, gelatin, nutrient broth, R2A and Luria-Bertani broth, minimal salts media, waste water comprising cellulose containing material, vegetable oil, inorganic salts, peat, clay, rice, bran, cellulose, pulp, woodchip, polyacrylamide and polystyrene, but not limited thereto.

In one embodiment, the microorganisms may be immobilised on a carrier such as for example, collagen, alginate, polyacrylamide and polystyrene, or may be microencapsulated. See for example Microbial Process Development, H. Doelle, World Scientific, 1994.

The microorganisms in one embodiment may be in lyophilised or freeze-dried form. These forms may be prepared using known art techniques, see for example Freeze-Drying/Lyophilization of Pharmaceutical and Biological Products by Rey and May (Eds), Informa Healthcare, January 2004, Drugs and Pharmaceutical Science Series, No. 2.

In one embodiment, the composition may comprise two, three or more bacterial strains of the invention.

In another aspect, the invention provides a method of degrading a cellulose containing material which method comprises treating the material with a composition of the invention or one or more microorganism strains of the invention effective to degrade cellulose. In one embodiment, two or three microorganism strains of the invention, or a composition comprising same are used in the method.

The cellulose containing material degraded by the bacterial strains of the invention encompasses a wide range of organic matter including but not limited to household waste, plants and plant parts including, wood, crops, and grasses; sewage, woodpulp from forestry or woodchip pulp, and waste from agriculture, forestry, and food processing generally. Examples include switchgrass, poplar, willow, miscanthus, sugar cane, corn, paper, cardboard, and cellulose fines from paper mills. The cellulose containing material commonly includes lignocellulose and hemicellulose. Any combination of two or more of these cellulose containing materials is also contemplated.

The method may be carried out as a batch, semi-batch, continuous or semi-continuous method or process.

The amount of microorganisms required to degrade the cellulose can be determined using known art methods. Typical effective amounts of microorganisms for degradation will be in the range $1 \times 10^3$ to $1 \times 10^{15}$, or $1 \times 10^5$ to $1 \times 10^9$, or $1 \times 10^6$ to $1 \times 10^7$ CFU/ml. The microorganisms or compositions containing same may be added in these amounts, or allowed to grow to a population in these ranges. In one embodiment the microorganisms or compositions of the invention may be added in batches.

The microorganisms may also be used in the method with, or the compositions of the invention may further comprise, other energy sources such as carbohydrates, sugars, fats, oils, alcohols, or mixtures thereof, and nutrients, vitamins, trace elements, and minerals useful or required for microbial growth.

Examples of energy sources include starch, glucose, galactose, maltose, mannose, fructose, sucrose, raffinose, xylose, rhammanose monohydrate, arabinose, ribose, cellobiose, trehalose, acetylglucosamine, di- and trisaccharides, cellulose and cellulose derivatives (for example, carboxymethyl cellulose and cellulosic pulp), methanol, ethanol, propanol, butanol, sodium pyruvate, sodium acetate, and sodium citrate.

For nutrients, yeast extract may be used. Vitamins typically include folic acid, vitamin B1, vitamin B2, niacin, niacinamide, pantothenate, pyridoxine, cobalamin, biotin, choline, inositol, and para-amino benzoic acid. Minerals typically include metals such as zinc, potassium, calcium, iron, copper, sodium, cobalt, magnesium, aluminium, nickel, manganese, and molybdenum and non metals such as phosphorous, boron, iodine and selenium. The minerals are commonly provided in salt form such as zinc sulphate, copper sulphate, manganese sulphate, manganese chloride, aluminium chloride, nickel chloride, cobalt chloride, sodium molybdate, sodium tungstate, iron ammonium sulphate, iron sulphate, sodium selenate, calcium chloride, sodium bicarbonate, potassium dihydrogen phosphate, ammonium sulphate, and boric acid, but are not limited thereto. The minerals may also be provided in the form of a solution that includes a chelater, such as sodium EDTA (disodium dihydrogen ethylenediaminetetraacetate) and nitrilotriacetic acid.

Vitamins, minerals and nutrients may be added in amounts required for microbial growth. The amounts can be readily determined by an art skilled worker. Generally, minerals and vitamins are added in trace amounts, generally 0.1 to 30 mg/L. Nutrient and/or growth factors added per se or as yeast extract are added in trace amounts, generally 10 to 100 mg/L.

Other additives in the compositions, or useful in the methods include for example, preservatives, surfactants, fillers, extenders, binders, buffing agents, colourants, anti-oxidants, odourants, spreaders, dispersants and wetting agents, acidulants, alginates, mannans, glycerol, polysaccharides, cellulose, xylans, pullulans, carageenans, carbohydrates, and those additives which assist in maintaining microorganism viability, for example corn oil, but not limited thereto.

The material to be degraded in the method or process is commonly contacted with the microorganism in an aqueous environment. The material may be comminuted prior to contact to facilitate degradation. Alternative forms of contact and other pretreatments known in the art are also contemplated.

The method is desirably carried out at temperatures between about 40 to 75° C. In one embodiment the method is carried out at about 60 to 70° C., or about 60° C. to 65° C.

Most usually, the method is carried out at a pH of between about 3.0 to 7.5, commonly between about 4.0 and 7.0, or about 3.5 to 6.5, or about 4.5 to 6.0 and in one embodiment at pH 5.0.

In one embodiment, the method is carried out under aerobic conditions.

The ability to degrade a wide range of cellulosic substances in a moderately acidic pH and at high temperatures is believed to be unique to these Chloroflexi-like species of the invention. Acid tolerant celluloses are a desirable trait for commercial biofuel operations. For example, the current method of pre-treatment of cellulosic substrates requires acidic-steam explosion treatment to delignify the cellulose fibers. Post-treatment, the liquor must be neutralised before hydrolysis with non-acid fast cellulolytic enzymes. The reduction in base addition achievable using Chloroflexi-like species of the invention may reduce operating costs.

Various aspects of the invention will now be illustrated in a non-limiting way by reference to the following experimental sections.

EXAMPLE 1

Isolation and Characterisation of Chloroflexi-Like Isolates T81, T26 and T12

Materials and Methods

Strains T81, T26 and T12 were obtained from volcanic soil obtained from Tikitere geothermal field at Hell's Gate in the Taupo Volcanic Zone in the North Island of New Zealand.

Tikitere is a geothermal area of neutral chloride waters (pH 7.2) rich in dihydrogen gas, methane and ammonia. Geothermal features in the Hell's Gate tourist park include mud volcanoes, hot springs, fumaroles and steaming soil. An area of soil covered by low shrubs that had recently died due to the onset of steam venting through the soil was selected. There was a steep temperature gradient through the vertical soil structure, which consisted of an undecomposed organic horizon (0-2 cm, 31° C. at 1 cm), an A horizon (2-5 cm, 42° C. at 3.5 cm), an iron-rich horizon (5-10 cm, 53° C. at 7.5 cm), black ash (10-15 cm, 63° C. at 12.5 cm) and white ash and pumice (below 15 cm, 71° C. at 17.5 cm).

Samples from 2-15 cm were used for inoculation of bacterial growth media.

Isolation of Bacteria:

The media used for isolation was a basal salts mixture (below) solidified 0.8%-1.5% phytagel (Sigma, Missouri, USA) with 2 g $L^{-1}$ $MgCl_2.6H_2O$.

Two basic mineral salts media, FS3V and AOM1, were used for the enrichment and isolation process.

Mineral salts medium FS3V contained (per L): 0.4 g $NH_4Cl$; 0.1 g $KH_2PO_4$; 0.04 g $MgSO_4.7H_2O$; 0.02 g $CaCl_2.6H_2O$; 6 ml FeEDTA solution (see below), 6 ml of trace elements 1 solution (see below) and 2 ml of trace elements 2 solution (see below). The medium was adjusted to a pH of 4.5 using dilute HCl. The media were solidified by adding 15 g $L^{-1}$ of phytagel plus 1 g $L^{-1}$ of $MgCl_2.6H_2O$ (at pH 4.5). The phytagel (gellan) served as both a solidifying agent and a potential energy source for chemotrophic growth. One hundred mg $L^{-1}$ of a vitamin mixture (see below) and 100 mg $L^{-1}$ yeast extract was also added through a 0.2 μm fitter after autoclaving to this medium.

The FeEDTA solution contained (per L): 1.54 g $FeSO_4.7H_2O$; 2.06 g $Na_2EDTA$. Trace elements solution 1 contained (per L): 0.44 g $ZnSO_4.7H_2O$; 0.20 g $CuSO_4.5H_2O$; 0.19 g $MnCl.4H_2O$; 0.06 g $Na_2MoO_4.2H_2O$; 0.10 g $H_3BO_3$; 0.08 g $CoCl_2.6H_2O$. Trace elements solution 2 contained (per L): 1.5 g nitrilotriacetic acid; 0.2 g $Fe(NH_4)_2(SO_4)_2.6H_2O$; 0.2 g $Na_2SeO_3$ 0.1 g $CoCl_2.6H_2O$; 0.1 g $MnSO_4.2H_2O$; 0.1 g $Na_2MoO_4.2H_2O$; 0.1 g $Na_2WO_4.2H_2O$; 0.1 g $ZnSO_4.7H_2O$; 0.04 g $AlCl_3.6H_2O$; 0.025 g $NiCl_2.6H_2O$; 0.01 g $H_3BO_3$ 0.01 g $CuSO_4.5H_2O$ (pH 7). The vitamin mixture contained (in 100 mg): 0.8 mg folic acid; 8 mg vitamin B1; 4 mg vitamin B2; 1 mg niacin; 10 mg niacinamide; 15 mg pantothenate; 15 mg pyridoxine; 5 mg cobalamin; 5 mg biotin; 15 mg choline; 15 mg inositol; 7 mg para-amino benzoic acid.

Medium AOM1 (pH 6.5) contained (per L) 4 g $NH_4SO_4$; 0.25 g $NaHCO_3$ 0.05 g $KH_2PO_4$; 0.666 g $MgSO_4.7H_2O$; 5 mg $CaCl_2.6H_2O$; 10 mg yeast extract, 10 mg vitamins, 1 ml FeEDTA solution (see above), 1 ml of trace elements solution 2, and 15 g $L^{-1}$ of phytagel.

Soil crumbs were spread on plates and these were incubated at 60° C. In most cases incubations were carried out in sealed jars or desiccators supplemented with 5-10% v/v $CO_2$. Plates were viewed after 3-4 days and then at 1-week intervals for at least 4 weeks. Colonies that formed around soil crumbs within 4 weeks were restreaked onto new medium. Individual colonies growing from these secondary streaks (within 4 weeks) were selected with the aid of a stereo microscope and serially streaked onto new plates until pure cultures were obtained.

Characterization of Isolates:

Novel isolates were characterized morphologically via phase-contrast tight microscopy. Cells were fixed for transmission electron microscopy (Zeiss LEO 912 Energy-Filtering TEM), and scanning electron microscopy (Hitachi S-800 FESEM) as previously described (Weatherby and Lenz (2000), *Arth Struct Devel*, 29: 275-288.). Some isolates were tested for growth on gellan as the sole energy substrate by comparing growth in a liquid version of the appropriate mineral salts medium they were isolated on (see previous section) containing either no added gellan or 1% (w/v) gellan. Additional characterization of novel isolates is described below in Example 3.

The Chloroflexi-like isolates were also characterized for maximum growth temperatures, pH range, $CO_2$ requirement and ability to grow on a variety of complex carbohydrates and defined organic media (Table 2). The pH and temperature ranges and $CO_2$ requirements were tested using the FS3V medium, pH 4.5+5% v/v $CO_2$ with 1% w/v gellan, as the basal media. Where the isolates were tested for their requirement for additional $CO_2$, active culture were inoculated into basal medium containing either 10% v/v $CO_2$ in air or air with no additional $CO_2$. The pH ranges of isolates were determined by adjusting to the desired pH with either HCl or NaOH. The Chloroflexi-like isolates were also grown in medium FS3V+ 5% v/v $CO_2$ containing 0.5 g $L^{-1}$ of either gellan, xanthan, pectin, xylan, carboxymethylcellulose or sodium alginate to test for growth on complex carbohydrates. Bacto agar (Difco Microbiology, Kansas, USA) was used as a negative control. In addition, all isolates were tested for growth on defined complex nutrient media including R2A (Reasoner and Geldreich (1985) *Appl Environ Microbial*, 49:1-7), nutrient broth (Sigma, Missouri, USA), tryptic soy broth (Merck, New Jersey, USA) and Luria-Bertani (Merck) broth. These media were adjusted to pH 5.5 for Chloroflexi using dilute HCl and then autoclaved. All tests were conducted at 60° C. Catalase production was evaluated qualitatively by determining the appearance of bubbling after a few drops of freshly prepared 3% hydrogen peroxide were added to a centrifuged culture grown on liquid medium. Alkaline and acid phosphatase production was determined using Api®ZYM kits (BioMerieux, North Carolina, USA) according to the manufacturer's instructions.

Molecular Analyses:

Pure cultures were aseptically transferred to sterile extraction tubes and extracted using the FastDNA SPIN kit (Q-BIOgene, MP Biomedicals, California, USA) as per the manufacturer's instructions. Environmental DNA was extracted from soil samples via a mechanical disruption protocol using the FastDNA SPIN Kit for Soil (Q-BIOgene, Supra). The 16S rRNA genes from pure cultures and soil extracts were amplified using the primer pairs 9f and 1492b (Weisberg et al (1991). *J Bacterial* 2: 697-703.). The PCR mixture contained $1 \times NH_4^+$ PCR buffer (BIOLINE, Massachusetts, USA), 1.5 mM $MgCl_2$, 0.5 mM dNTP and 1 μL of Taq polymerase (BIOLINE, Supra). 16S rRNA gene products from soil extracts were cloned into *E. coli* using the TOPO TA cloning kit (Invitrogen, California, USA). Positive clones were selected and transferred into PCR cups for a direct PCR amplification using M13 primers. PCR products were purified using the PureLink PCR Purification Kit (Invitrogen, Supra) and then sequenced using BigDye terminator chemistry (Applied Biosystems, California, USA) on an ABI 373OXL capillary DNA sequencer.

Sequences were subject to a discontiguous megablast search against the NCBI database in order to identify the most closely related organisms. Potential chimeric sequences were eliminated by comparison of alignments of the 3' and 5' ends, and by the chimera check program Bellerophon (Huber et al. (2004) *Bioinformatics* 20: 2317-2319.). Non-chimeric sequences were then aligned to other 16S rRNA sequences using the ARB phylogeny software (Ludwig et al. (2004) *Nucleic Acids Res*, 32:1363-1371.) and the 2007 ARB-Silva database (release SILVA-89) (http:/www.arbsilva.de/). Phylogenetic trees were constructed using the FastDNAml maximum likelihood algorithm in the ARB software environment.

Results

Isolation of Bacteria:

The cultivated bacteria are listed in Table 2 discussed below.

Phylogenetic analysis assigned isolates from Tikitere to the candidate phylum Chloroflexi-like (Table 1, FIG. 1).

TABLE 1

Similarity matrix showing percentage sequence similarity between T81, T12 and T26, and other closely related cultured *Chloroflexi* and *Chloroflexi*-like species. Table was generated using Neighbour-joining algorithm in the ARB software environment.

| | 1 | 2 | 3 | 4 | 5 | 6 | 7 | 8 | 9 | 10 |
|---|---|---|---|---|---|---|---|---|---|---|
| 1. *Herpetosiphon aurantiacus* AATI01000064 | 100 | | | | | | | | | |
| 2. *Chloroflexus aggregans* AAUI01000024 | 77.2 | 100 | | | | | | | | |
| 3. *Roseiflexus castenholzii* AAUM01000026 | 79 | 83.1 | 100 | | | | | | | |
| 4. *Sphaerobacter thermophilus* AJ420142 | 76.4 | 76.3 | 75.4 | 100 | | | | | | |
| 5. *Dehalococcoides* sp. BHI80-52 AJ431247 | 72 | 72.8 | 74 | 76.4 | 100 | | | | | |
| 6. *Ktedonobacter racemifer* AM180156 | 71.6 | 70.6 | 72.8 | 75.5 | 73.9 | 100 | | | | |
| 7. *Chloroflexi bacterium* Ellin7237 AY673403 | 69 | 70.7 | 72.8 | 76 | 73.3 | 78.9 | 100 | | | |
| 8. T81 | 71.8 | 71.3 | 75.6 | 76.6 | 73.4 | 80.2 | 77.9 | 100 | | |
| 9. T12 | 71.9 | 71.4 | 75.1 | 76.7 | 72.9 | 80.3 | 77.3 | 98.3 | 100 | |
| 10. T26 | 72 | 71.3 | 75.2 | 76.9 | 73.1 | 80.7 | 77.8 | 98.8 | 99.2 | 100 |

The isolates were Gram-positive, filamentous bacteria that produced spore clusters and grew on a variety of complex medium and carbohydrates (Table 2) as follows:

TABLE 2

Morphological and physiological characteristics of representative isolates from the phylum Chloroflexi

| | Isolate T81, T26, T12[a] |
|---|---|
| Phylum | Chloroflexi |
| Gram stain | + |
| Cell form | Filamentous with branching hyphae |
| Colony morphology | White, vegetative and aerial mycelia |
| Cell dimensions (w, d) | 0.2-0.4 μm, +30 μm |
| Spore formation | + |
| Motility | − |
| Maximum growth temperature | 75° C. |
| pH (range) | 4.0-7.5 |
| Catalase | − |
| Alkaline phosphatase | + |
| Acid phosphatase | + |
| Growth on mineral medium[b] | |
| Agar | + |
| Gellan | + |
| Phytagel | + |
| xanthan | + |
| carboxymethylcellulose | + |
| Xylan | +/− |
| Avicel | + |
| Pectin | + |
| sodium alginate | + |
| Growth on defined nutrient media[c] | |
| R2A | + |
| NB | + |
| TSB | + |
| LB | + |
| Requirement for $CO_2$ | − |

[a]in further experiments (Example 3), the energy sources that support growth for individual strains was further investigated and in some cases, adjusted to reflect differing medium conditions
[b]mineral medium FS3V, +5% v/v $CO_2$ pH 4.5
[b]NB, nutrient broth; TSB, tryptic soy broth; LB, Luria-Bertani Cells were about 0.4 μm in diameter and single cell filaments >30 μm were observed. These were frequently branched without septa, but occasional septa-like cell divisions were observed connecting individual cells in filaments. Newly developing branches were usually characterized by an electron-dense region in the branching tip.

The phylum Chloroflexi is extremely diverse phenotypically (Hanada and Pierson (2002), The family Chloroflexaceae. In The Prokaryotes: an Evolving Electronic Resource for the Microbiological Community 3rd edn (release 3.11, Nov. 22, 2002, Edited by M. Dworkin, S. Falkow, E. Rosenberg, K-H. Schleifer & E. Stackebrandt. New York: Springer). If the Thermomicrobia are included as a class of Chloroflexi (Hugenholtz. P, and Stackebrandt, E. (2004), *Int J Syst Evol Microbiol* 54: 2049-2051) there are eleven recognized genera, which include thermophiles and mesophiles, phototrophs and chemotrophs, autotrophs and heterotrophs, aerobes and anaerobes, Gram-positives and Gram-negatives. While this phylum is extremely diverse, only a minimal number of isolates have so far been described. Here we provide and describe novel Chloroflexi-like isolates that are phylogenetically distinct from the all other Chloroflexi species so far isolated. *Sphaerobacter thermophiles* is the closest isolate from the phylum Chloroflexi with a 16S rRNA gene sequence similarity of ~80% 16S rRNA (Table 1). This *Chloroflexus* species possess minimal physiological and morphological traits with T81, T26 or T12 (Hugenholtz. P, and Stackebrandt, E. (2004) *Int J Syst Evol Microbiol* 54: 2049-2051). Our Chloroflexi-like isolates share slightly higher 16S rRNA sequence similarities (~81%) with to the recently described filamentous mesophilic soil bacteria, "*Ktedonobacter*" (Cavaletti et al. (2006), *Appl Environ Microbiol* 72: 4360-4369). Like "*Ktedonobacter*", the T81, T26 and T12 were aerobic, moderately acidophilic, Gram-positive, filamentous cells producing branched mycelia and spore clusters. However, the microorganisms of the invention had a much higher temperature limit (75° C.) and were also more adept at utilising a wide range of substrates as energy sources including complex nutrient medium and complex carbohydrates such as cellulose (Table 2), which makes them similar to other members of the Chloroflexi. Their substantial phylogenetic dissimilarity with all other bacteria suggests that they may be a novel class and perhaps even a novel phylum of bacteria. Currently these isolates are being classified as belonging to the phylum Chloroflexi. However, as noted above, if "*Ktedonobacter*" are ultimately classified as a new phylum then the isolates belong more closely to this phylum than the Chloroflexi-like.

EXAMPLE 2

The ability of the Chloroflexi-like isolates to degrade cellulose was tested using a variation of a method as described by Lai et al., (2006), *Talanta,* 69: 68-72. Isolates were inoculated into sterile 50 mL AOM1 medium (pH 5.0) containing 0.6 g $L^{-1}$ cellulose azure (Sigma, Supra, C1052) in place of Phytagel, and a headspace containing 2% v/v $CO_2$ in air. Experiments were conducted in duplicate at 60° C. and shaking at 140 rpm. The degradation of cellulose was detected spectrographically by the release of the azure pigment from the cellulose azure at an optical density of 595 nm. Samples were taken aseptically at 24 hour intervals, centrifuged at 14,000 rpm to remove bacteria, prior to measuring optical density. Also included in the experiment were two sets of controls; one positive control to confirm cell viability (AOM1), and a non-inoculated negative control to account for non biological release of the azure pigment.

Figure 3:
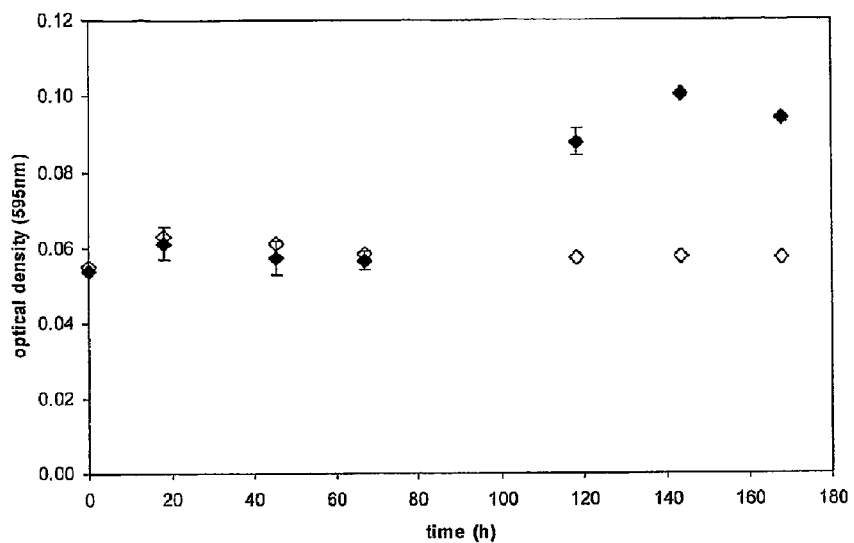
FIG. 3 demonstrates cellulose utility by Chloroflexi-like isolate T81 as measured by the release of azure (OD=595 mm).
Figure 4:
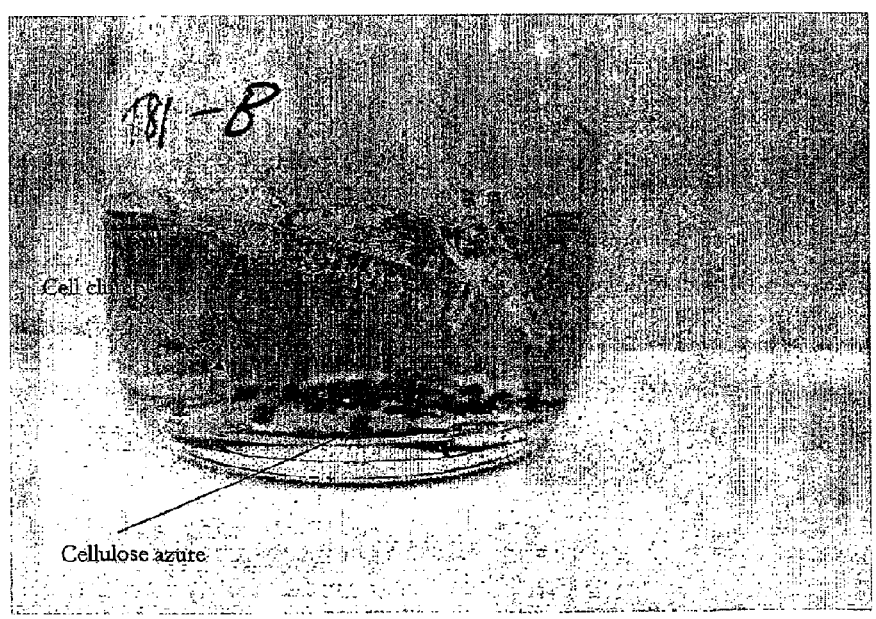
FIG. 4 is a digital camera image of Chloroflexi-like isolate T81 during a cellulose degradation experiment. The image shows the azure colour released during the degradation of cellulose azure (deep black clumps) by T81 (light grey clumps).

The utilization of cellulose by the Chloroflexi-like isolates (T81) is shown in FIG. 3, via the release of azure (OD=595 nm) from cellulose azure. More azure was released from the substrate than the inoculated control, and the utilisation of cellulose- and hemicellulose-like substrates such as Phytagel, gellan, carboxymethylcellulose, xanthan, xylan, pectin, Avicel® and sodium alginate as their sole energy source. These data clearly show the release of azure in the inoculated vials as compared to the non-inoculated controls, and therefore cellulose utilisation. As the isolate grows in unusual mycelia-like clumps and not a homogenous cell suspension, the corresponding cell density increase (OD=600 nm) was unable to be demonstrated. However, in place of an optical density measurement, a digital camera image was taken to demonstrate growth (FIG. 4).

It is currently believed that the isolates will degrade cellulose at temperatures as high as 75° C., equalling or bettering the highest known temperature for an aerobic cellulose-degrading thermophile (currently *Rbodothermus marinus*).

EXAMPLE 3

Additional Characterization of *Chloroflexus* Strains

Further characterization of *Chloroflexus* strains was carried out to elucidate the ability of *Chloroflexus* strains to degrade cellulose and cellulose-based substrates as well as the potential of these strains to be used in the cellulose to ethanol conversion process. Three strains were selected for these analyses, T81, T26 and T12 as described above.

Materials and Methods

Growth Media

Mineral salts medium FS3V, FeEDTA, Trace elements solution and AOM1 medium were prepared as for Example 1. Energy sources were added to both media prior to autoclaving (0.5 g/L), except where noted, via syringe filter.

Solidified media was made by amending AOM1 or FS3V with 15 g/L of Phytagel® or 15 g/L of Phytagel® and 1 g/L $MgSO_4.7H_2O$ respectively, prior to autoclaving.

Unless otherwise stated, the following growth conditions were used for all experiments; *Chloroflexus* strains were grown aerobically at 60° C. in capped 100 mL serum bottles containing 50 mL of medium and 50 mL air headspace. No $CO_2$ was amended to the headspace. Medium was sterilised via autoclaving (121° C., 20 min). Fifty µL of culture was inoculated into 50 mL of sterile medium. Stock *Chloroflexus* strains were maintained in liquid culture on mannose and on carboxymethylcellulose (CMC), and on phytagel-based solid medium.

HPLC Operating Conditions

Unless otherwise stated, sugars and/or alcohols were measured on a Dionex Ultimate 3000® High Performance Liquid Chromatography (HPLC) unit via refractive index (RI) on a Shodex RI-101 unit (Dionex, Utah, USA). The RI unit was run at 35° C. Samples (10 µL) were injected into a degassed water carrier solution running at 0.6 mL/min. Samples were separated on a Varian PL Hi-Plex H (8 µm, 300×7.7 mm) at 60° C. (Varian, Massachusetts, USA). Chromatographs were interpreted using Chromeleon® software (Dionex, Utah, USA).

Metabolism Experiments

Growth experiments to determine growth using different energy sources were conducted using the basal media, AOM1 or FS3V. No yeast extract (YE) or vitamins were added as growth supplements to either medium in these series of experiments. Preliminary experiments have shown that they are not required. Both the YE and vitamin mix were also tested as sole energy sources.

Sole energy sources were added at a concentration of (0.5 g/L). The following cellulose-based compounds were tested; gellan (Sigma, Missouri, USA, G1910), phytagel (Sigma, P1869), agar (Becton Dickinson, New Jersey, USA, 214010), chitin (Sigma, C7170), carboxymethylcellulose (Hercules, Delaware, USA, AQUALON®), xylan (Sigma, X4252), pectin (CP Kelco Ltd, Surrey, UK, type 115), xanthan (CP Kelco Ltd), sodium alginate (Aldrich, Missouri, USA, 180947), Avicel® (Fluka, Missouri, USA, 11365), starch (Sigma, S9765), cellulose filter paper (Whatman, USA, Type 41 Ashless), dextrin (Sigma, D2006), pullulan (Fluka, 70074) and glycogen (Sigma, G0885)1, Monosaccharides tested include D-glucose (Fluka, 49139), D-fructose (Sigma, F0127), D-galactose (Sigma, G0750), D-raffinose pentahydrate (Fluka, 83400), D-galacturonic acid (Fluka, 83400), D-ribose (Sigma, R7500), D-mannose (Sigma, M5895), DL-arabinose (Sigma, A9524), xylose (Sigma, X1500), L-rhamnose monohydrate (Sigma, R3875) and D-N-actetylglucosamine (Aldrich, A1.628-9), Disaccharides include sucrose (Fluka, 84097), D-maltose (Fluka, 63582), D-cellobiose (Fluka, 25150), D-trehalose (Sigma, T0167), The growth of Strain T12 on D-mannose in AOM1 medium with a lower pH (pH4.5) was also tested. Yeast extract (Becton Dickinson, 211929), sodium pyruvate (Sigma, P2256), sodium citrate (Ajax Finechem, A467,) and sodium acetate (Sigma, S2881), were also tested as sole energy sources, along with the alcohols methanol (Merck, 1.06018), ethanol (Merck, 1.00983), 1-propanol (Merck, 1.01024), 2-propanol (Merck, 1.01040), pentanol (Sigma, 138975) and butanol (Sigma, 1.01988). A vitamin mix was tested as a sole energy source. The vitamin mixture contained (in 100 mg): 0.8 mg folic acid; 8 mg vitamin B1; 4 mg vitamin B2; 1 mg niacin; 10 mg niacinamide; 15 mg pantothenate; 15 mg pyridoxine; 5 mg cobalamin; 5 mg biotin; 15 mg choline; 15 mg inositol; 7 mg para-amino benzoic acid and was tested at 10 and 100 mg/L.

Experiments were inoculated using stock cultures of T81, T12 and T26 grown in a corresponding medium with a corresponding energy source type. For example, inoculum for testing growth on a cellulose-based compound was grown in the corresponding medium with a cellulose-based compound as an energy source. All energy sources were added at a concentration of 0.5 g/L prior to autoclave sterilisation, except for D-N-acetylglucosamine, D-(–)-fructose, sodium acetate, sodium citrate, sodium pyruvate, methanol, ethanol, 1-propanol, 2-propanol, pentanol and butanol which were added via filter sterilisation (0.22 µm pore size membrane syringe filter). Tests were conducted in triplicate with a sterile control. Bacterial growth was determined visually as optical density (OD) measurements are not possible due to growth characteristics of the Chloroflexi isolates.

All strains were tested for fermentative growth using Avicel®, CMC, glucose or cellobiose as sole energy source. Sterile FS3V medium was asceptically degassed then sparged with dinitrogen gas. Approximately 50 µL of $Na_2S$ (10 mM) was added to each 50 mL bottle to consume any remaining oxygen prior to inoculation.

Ethanol Toxicity

All three *Chloroflexus* strains were tested for their ability to grow on elevated levels of ethanol. Ethanol at concentrations of 0.1%, 1.0%, 2.0%, 5.0%, 7.5%, and 10.0% (v/v) were asceptically added into FS3V medium following sterilisation as the sole energy source. Strains were then inoculated and incubated statically.

Strain T81 was also tested for it's preference for alcohols over saccharides. Fructose (0.05% w/v) was added to FS3V medium containing either 0.05° A) or 5.0% (v/v) ethanol. Strain T81 was inoculated and incubated statically at 60° C. One milliliter samples were taken daily and frozen for analysis using HPLC.

pH and Temperature Ranges Evaluation

*Chloroflexus* strain T81 was tested for its optimal pH and temperature growth conditions. For testing the pH growth range, basal FS3V medium was distributed into 100 mL serum bottles with either mannose or starch as sole energy sources (0.05% w/v). The medium for a range of acidities (pH 2.5-8.0) was adjusted with dilute HCl prior to sterilisation. After cooling, the medium pH was re-measured to allow for any changes in acidity as a result of sterilisation. Strain T81 was inoculated into individual vials and incubated statically at 60° C. The pH optima and range was determined visually by the extent of biomass formation. For testing optimal temperature ranges, strain T81 was inoculated into FS3V medium with starch or mannose as sole energy sources and incubated statically at 37° C., 45° C., 50° C., 60° C., 65° C., 70° C. or 75° C. Like the determination of pH optima, optimal growth temperature was determined visually by the extent of biomass formation.

Molecular Detection of Other Metabolism Types

PCR amplification was used to screen for a selection of functional genes including dsrA encoding the α-subunit of dissimilatory sulfite reductase (DSR1F/DSR4R Wagner et al. (1998) *J. Bacteriol.* 180: 2975-2982.), pmoA encoding a subunit of particulate methane monoxygenase (189f/682r Holmes et al. (1995) *FEMS Microbiol. Lett.* 32: 203-208 and 189f/mb661 (Klob et al., (2003) *Appl. Environ. Microbiol.* 69(5):2423-2429), mcrA encoding methyl coenzyme M reductase (ME1/ME2 & AOM39_f/AOM40_r (Hallam et al. (2003) *Appl. Environ. Microbiol.* 69(9):5483-5491) and MCRf/MCRr (Lueders et al. (2001) *Environ. Microbiol.* 3(3): 194-204(11)) and coxL encoding the large subunit of aerobic carbon monoxide dehydrogenase (OMPf/O.Br (Dunfield and King (2004) *Appl. Environ. Microbial . . .* 70(7):4242-4248. These genes are an indication of sulfite/sulfate reduction (dsrA), aerobic methanotrophy (pmoA), anaerobic methane oxidation (mcrA), methanogenesis (mcrA) and aerobic carbon monoxide oxidation (coxL) respectively. The PCR protocol for each screening is described in detail in the corresponding references.

Detection of Extracellular Cellulase Activity

The presence of extracellular cellulase activity of T81 was investigated. T81 was grown for two weeks on either 0.05% (v/v) CMC, Avicel®, cellobiose or glucose in 50 mL FS3V medium. The T81 cells were then pelleted by centrifugation and frozen for later mass determination. The supernatant was transferred to sterile 100 mL serum bottles containing either CMC (CMC or glucose supernatant) or starch (Avicel® or cellobiose supernatant via a 0.22 μm syringe filter. The bottles were incubated statically at 60° C. One mL samples were taken every half-an-hour up until two hours, then hourly for eight hours after supernatant addition. Samples were also taken 22 and 28 hours following supernatant addition. Leachate samples were frozen to restrict further enzyme activity. Samples were analysed by HPLC. Negative controls containing sterile FS3V medium with either (0.05% (v/v) starch or CMC) were incubated under identical conditions and were sampled at times zero, eight, 28, 52 and 144 hours following medium addition.

Commercial Pulps

Cellulose pulp degradation and sugar generation by *Chloroflexus* strain T81 was assessed. A pre-inoculum culture of Strain 81 was initially was grown statically on using single pulp circles cut from a dried pulp mat. Once grown, it was inoculated into FS3V medium containing one of four examples of cellulose pulps as sole energy sources (0.05% wv) and incubated statically at 60° C. The pulps contained designated E90 (a NZ eucalyptus fully bleached kraft pulp—5-10% hemicellulose), BKT (a fully bleached radiata pine kraft pulp—containing about 10-15% hemicelluloses), K20 (an unbleached kraft pulp with a 3-4% lignin content) and a sample of a reslushed and fluffed pulp. Growth on the various pulp tablets was assessed visually.

Phylogenetic Position of *Chloroflexus* Isolates

Full length 16S rRNA gene sequences from the phylum *Chloroflexus* sequences were imported from the NCBI and the 2007 ARB-Silva database (release SILVA-89, http://www.arb-silva.de/). Potential chimeric sequences were eliminated by comparison of alignments of the 3' and 5' ends, and by the chimera check program Bellerophon (Huber et al., 2004). Non-chimeric sequences were then aligned to other 16S rRNA sequences using the ARB phylogeny software (Ludwig et al., 2004 *Nucleic Acids Res*, 32: 1363-1371.). Phylogenetic trees were constructed using the FastDNAml maximum likelihood algorithm in the ARB software environment. Phylogenetic trees were constructed using the TREE-PUZZLE, a quartet-puzzling maximum-likelihood algorithm in the ARB software environment. The tree was rooted against a group of seven sequences from other phyla, including *Synecoccus elongates* (D83715), *Arthrospira platensis* (DQ393280), *Alicyclobacillus acidocaldarius* (AB059663), *Geobacillus stearothermophilus* (AY608942), *Methylococcus capsulatus*(AE017282), *Methylosinus trichosporium* (AJ431385) and *Streptomyces halotolerans* (AY376166). Quartet-puzzling support values were generated using 10,000 resamples.

All thermophilic *Chloroflexus*-like isolates and clones detected in cultivation-independent surveys of geothermal environments in New Zealand were compared using the neighbour-joining method in a distance matrix. Likewise, selected thermophilic *Chloroflexus*-like isolates were with the closest related cultivated and non-cultivated species within the phylum Chloroflexi in a distance matrix as above.

Results

Metabolism Experiments

Figure 5:
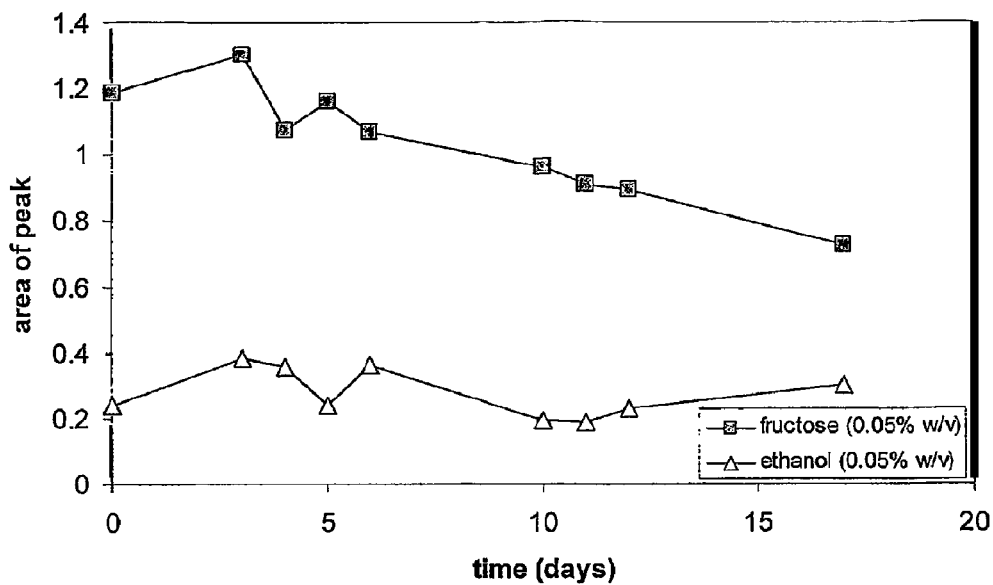
FIG. 5 shows the utilisation of fructose (0.05% w/v) in the presence of ethanol (0.05% w/v) for *Chloroflexus* strain T81.

Table 3 shows the growth of the three Chloroflexi isolates on different energy sources and on different basal medium. Generally, growth was superior on FS3V medium rather than on AOM1. In all cases, where growth was observed on AOM1, growth was also on FS3V medium, but the converse does not hold true. Growth for all three strains was greatest on starch, Avicel®, CMC, mannose, trehalose, cellobiose and pulp as the sole energy sources in the FS3V medium. Only galacturonic acid did not support growth of any of the isolates. Strain T12 was unable to grow on any sugars in the AOM1 (pH 6.5) medium. However, when tested in AOM1 medium adjusted to pH 4.5, Strain T12 was able to grow on mannose. T12 was the only strain capable of utilising dextrin as a sole energy source. All three Chloroflexi-like strains can grow on all tested alcohols with the exception of T12 on pentanol and butanol, and T81 on pentanol. The best growth for T81 and T26 on propanol, while T12 grows best on ethanol. When grown in the presence of ethanol (0.05% w/v) and fructose (0.05% w/v), strain T81 consumed fructose in preference to ethanol (FIG. 5). When grown in the presence of 5% (w/v) ethanol and 0.05% (w/v) fructose, the ethanol inhibited the growth of strain T81 and no fructose or ethanol was consumed (not shown).

Alcohol Toxicity

Table 3 shows the growth of the three strains on increasing ethanol concentrations. All strains were able to grow on ethanol concentrations of up to (and including) 2.0% (v/v). Strain T12 was able to grow on ethanol concentrations of up to (and including) 5.0% (v/v).

TABLE 3

Growth of *Chloroflexus* isolates T12, T26 and T81 on various sole energy sources in either AOM1 or FS3V medium. The isolates were grown under aerobic conditions at 60° C.

| | T12 | | T26 | | T81 | |
|---|---|---|---|---|---|---|
| Sole energy source | AOM1 | FS3V | AOM1 | FS3V | AOM1 | FS3V |
| phytagel | + | + | + | + | + | + |
| CMC | + | + | + | + | + | + |
| pectin | − | + | − | + | + | + |
| xanthan | − | + | + | + | + | + |
| xylan | − | + | + | + | + | + |
| Avicel ® | + | + | − | + | + | + |
| starch | + | + | + | + | + | + |
| sodium alginate | − | + | − | +/− | + | + |
| whatman filter paper | + | + | + | + | + | + |
| glycogen | − | + | − | + | + | + |
| chitin | − | +/− | − | +/− | − | +/− |
| dextrin | + | + | − | − | − | +/− |
| gellan | + | + | + | + | + | + |
| pullulan | + | + | + | + | + | + |
| Fluffed pulp | n.d. | + | + | + | + | + |
| K20 | n.d. | + | + | + | + | + |
| E90 | n.d. | + | + | + | + | + |
| BKT | n.d. | + | + | + | + | + |

TABLE 3-continued

Growth of *Chloroflexus* isolates T12, T26 and T81 on various sole energy sources in either AOM1 or FS3V medium. The isolates were grown under aerobic conditions at 60° C.

| Sole energy source | T12 | | T26 | | T81 | |
|---|---|---|---|---|---|---|
| | AOM1 | FS3V | AOM1 | FS3V | AOM1 | FS3V |
| YE + vitamins (100 mg/L) | − | + | + | + | + | + |
| YE + vitamins (10 mg/L) | n.d. | + | n.d. | + | n.d. | + |
| YE (10-100 mg/L) | n.d. | + | n.d. | + | n.d. | + |
| vitamins (10-100 mg/L) | n.d. | + | n.d. | + | n.d. | + |
| D-glucose | − | + | + | + | + | + |
| D-(+)-maltose | − | + | − | + | + | + |
| D-(−)-fructose | n.d. | + | − | + | + | + |
| D-(+)-galactose | − | − | − | + | + | + |
| D-(+)-mannose | − | + | − | + | + | + |
| D-(+)-arabinose | − | + | − | + | − | + |
| D-(+)-xylose | − | + | − | + | + | + |
| L-rhamnose monohydrate | − | + | + | + | + | + |
| D-(−)-ribose | n.d. | + | − | + | − | + |
| D-(+)-cellobiose | − | + | + | + | + | + |
| D-(+)-trehalose | − | + | − | + | + | + |
| sucrose | − | + | + | + | + | + |
| raffinose | − | + | − | + | + | + |
| D-N-acetylglucosamine | − | + | + | + | + | + |
| galacturonic acid | − | − | − | − | − | − |
| methanol (0.05% v/v) | n.d. | + | n.d. | + | n.d. | + |
| ethanol (0.05% v/v) | n.d. | + | n.d. | + | n.d. | + |
| 1-propanol (0.05% v/v) | n.d. | + | n.d. | + | n.d. | + |
| 2-propanol (0.05% v/v) | n.d. | + | n.d. | + | n.d. | + |
| 1-pentanol (0.05% v/v) | n.d. | n.d. | n.d. | + | n.d. | n.d. |
| butanol (0.05% v/v) | n.d. | n.d. | n.d. | + | n.d. | + |
| ethanol (0.1% v/v) | n.d. | + | n.d. | + | n.d. | + |
| ethanol (1.0% v/v) | n.d. | + | n.d. | + | n.d. | + |
| ethanol (2.0% v/v) | n.d. | + | n.d. | + | n.d. | + |
| ethanol (5.0% v/v) | n.d. | + | n.d. | − | n.d. | − |
| ethanol (7.5% v/v) | n.d. | n.d. | n.d. | − | n.d. | − |
| ethanol (10% v/v) | n.d. | n.d. | n.d. | − | n.d. | − |
| sodium pyruvate | n.d. | + | n.d. | + | n.d. | + |
| sodium acetate | n.d. | + | n.d. | + | n.d. | + |
| sodium citrate | n.d. | + | +/− | − | +/− | − |

YE; yeast extract,
n.d.; not determined,
E90; a NZ *eucalyptus* fully bleached kraft pulp - 5-10% hemicellulose,
BKT; a fully bleached radiata pine kraft pulp containing in the order of 10-15% hemicelluloses,
K20; an unbleached kraft pulp with a 3-4% lignin content pH and Temperature Ranges Evaluation

Figure 6:
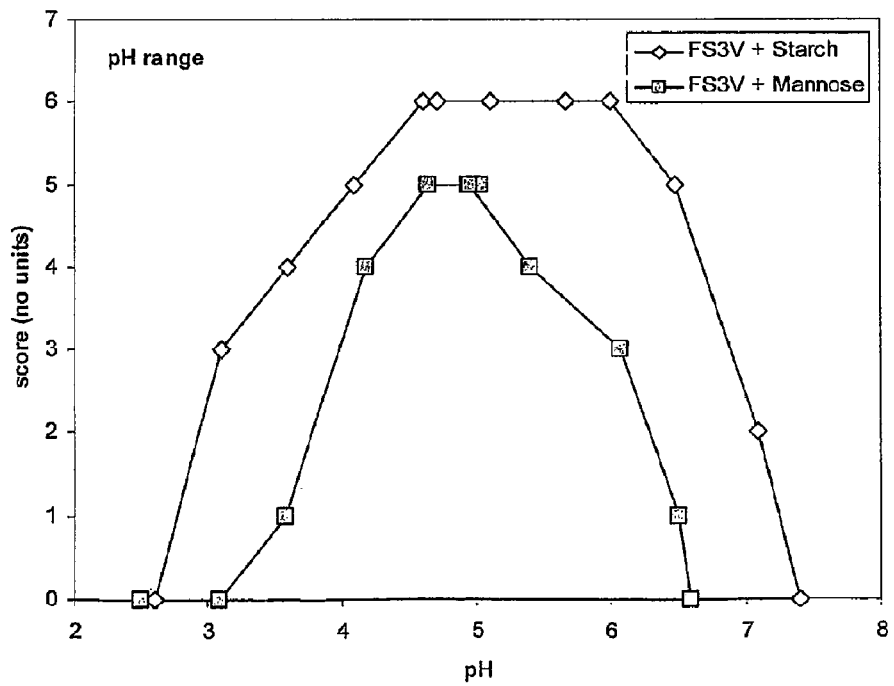
FIG. 6 shows the pH growth range for *Chloroflexus* strain T81. The pH optima and range was determined visually and given a score by the extent of biomass formation.

FIG. 6 and Table 4 show the pH and temperature ranges for T81. The best growth was observed between pH 4.5 and 6.0, with the lower pH limit being pH 3.0 for starch and pH 3.5-4.0 for mannose. The optimal temperature for T81 was 60-65° C. with a temperature growth range of 45-75° C. for growth on mannose and starch.

TABLE 4

Temperature and pH optima for *Chloroflexus* strain T81

| | *Chloroflexus* strain T81 | |
|---|---|---|
| | pH$_{opt}$ (pH range) | Temp$_{opt}$ (temp range) |
| Mannose | 4.6-5.0 (3.5-6.5) | 60-65° C. (45-75° C.)[a] |
| Starch | 4.6-6.0 (3.1-7.4) | 60-65° C. (45-75° C.)[a] |

[a]note that in this set of experiments 40° C. was not tested. However, 40° C. did support the growth of all strains as reported in Example 1.

Molecular Detection of Other Metabolism Types

All metabolism types tested using primers designed to target functional genes were negative using the selected primer pairs. These included DsrA (dissimilatory sulfite reductase), PmoA (particulate methane monooxygenase), CoxA (aerobic carbon monoxide dehydrogenase) and McrA (methanogenesis and anaerobic methanotrophy). As will be understood by those of skill in the art, functional genes including or related to DsrA, PmoA, CoxA and McrA may still be present in the organisms tested due to primary sequence divergence.

Detection of Extracellular Cellulase Activity

Extracellular activity was assessed by the generation of glucose from CMC or starch incubations. No extracellular cellulose activity was detected in any of the samples using the methods described above.

Commercial Pulps

Growth was observed on all commercial pulps by all strains in all media with the exception of T12 in AOM1 medium. The Chloroflexi-like cells formed mycelial tufts on the surface of the cellulosic tablets (see FIG. 9).

Phylogenetic Position of *Chloroflexus* Isolates

The phylogenies of thermophilic *Chloroflexus*-like strains were compared. These included strains T81, T104, T12, T26 and T24 from isolated from Tikitere geothermal field and strains P352, P359 and P353 isolated from Waikite geothermal fields. Also included in the analysis were several clones detected in molecular surveys of geothermal in these two geothermal fields. The distance matrix data presented in FIG. 7 show that the thermophilic *Chloroflexus*-like strains has the greatest 16S rRNA gene sequence dissimilarity between strains P359 and T81 of 3.5%. The two strains with the closest sequence similarity are between strains T104 and T24 of only 0.1%.

The thermophilic *Chloroflexus*-like strains formed a Glade phylogentically distinct from all other members of the phylum Chloroflexi (FIG. 1 and FIG. 7). Quartet-support puzzling-values for this Glade were greater than 99%. The most closely-related phylotype outside this Glade was a grassland soil clone, (EU044277) with strain P359 of 83.1% and a c-horizon soil clone (EU335405) with strains T12 and T26 of 83.1 and 83.2% respectively. The most closely related cultivated strain was *Ktedonobacteria* sp., SOSP1-0 (AM180153) with strain T26 (81.0%).

Discussion

The experiments reported in this example provide experimental data on the cellulolytic ability of thermophilic *Chloroflexus* strains T81, T26 and T12.

The metabolic data indicates that *Chloroflexus* strains T81, T26 and T12 have a broad ability to utilise a wide variety of organic compounds. In particular, the strains were able to derive energy from every complex and simple saccharides tested with the exception of galacturonic acid.

Without being bound by any particular theory, the inventors believe that this ability demonstrates that these strains have a primarily cellulosic lifestyle. While complex polysaccharides such as cellulose or starch do not directly support microbial growth, the ability to hydrolyse a broad spectrum of polysaccharides into useable short mono- or disaccharides such as glucose or cellobiose gives these *Chloroflexus* strains a competitive advantage in mixed environments. Interestingly, Strain T12 was unable to utilise sugars for growth at near neutral pHs. However, when tested in AOM1 medium (pH 4.5), the strain was able to grow on mannose. In addition, the ability to utilise alcohol (the by-product of saccharide fermentation) further enhances the ability of these strains to benefit from it's cellulolytic activity.

The data presented clearly show that the tested strains grow rapidly on a broad range of cellulosic substrates (including Avicel®—see FIG. 10). Avicel is a non-soluble cellulose substrate that is recalcitrant to hydrolysis. The ability of the strains to hydrolyse a broad range of celluloses including Avicel® indicates the Chloroflexi are therefore useful in cellulosic leaching systems, and in the production of bioethanol from cellulose.

The inventors also believe that the ability of the tested strains to degrade cellulose at a moderately acidic pH range and high temperatures is novel, particularly for a thermophilic bacterium.

The *Chloroflexus* strains of the invention may be classified by molecular phylogenetics in the phylum *Chloroflexus*. The most closely related cultured species, *Ktedonobacter racemesis* (81% sequence similarity) has been classified as a novel class of bacterium Ktedonobacterales (Euzeby, (2007) *Int. J. Syst. Eva. Microbiol.* 57: 433-434). However, the phylogenetic data presented here suggests that the thermophilic *Chloroflexus*-like strains studied are phylogentically distinct from that of the Ktedonobacterales and most probably represent a separate novel class of the Chloroflexi.

The inventors have shown that the *Chloroflexus* strains of the invention have a broad pH range under which cellulolytic activity was observed. This ability to operate at moderately acidic pH's has not been previously demonstrated for such organisms. The inventors have also shown that the *Chloroflexus* strains have high temperatures of operation, broad substrate specificity (especially for cellulosic compounds), and a high tolerance to elevated concentrations of ethanol which may make them useful in the processes for producing ethanol from cellulose. As noted in the background, conversion of biomass to ethanol is a three step process. The *Chloroflexus* strains have demonstrated utility in step 2 of that process which requires cellulose hydrolysis.

It will be appreciated that the above description is provided by way of example only and that variations in both the materials and techniques used, which are known to those persons skilled in the art, are contemplated.

Additional Indications

Australia

The applicant hereby gives notice that the furnishing of a sample of a microorganism shall only be effected prior to grant of a patent, or prior to the lapsing, refusal or withdrawal of the application, to a person who is a skilled addressee without an interest in the invention (Regulation 3.25(3) of the Australian Patents Regulations.

Canada

The applicant hereby requests that, until either a Canadian patent has been issued on the basis of the application or the application has been refused or abandoned and no longer subject to reinstatement, or is withdrawn, the furnishing of a sample of deposited biological material referred to in the application only be effected to an independent expert nominated by the Commissioner of Patents.

Croatia

The applicant hereby requests that the samples, upon request, be made available between the publication of the application and the granting of the patent to anyone requesting them, or, if the applicant so requests, only to an independent expert, or to, after the patent has been granted, and notwithstanding cancellation or revocation of the patent, anyone requesting them.

Denmark

The applicant hereby requests that, until the application has been laid open to public inspection (by the Danish Patent and Trademark Office), or has been finally decided upon by the Danish Patent and Trademark Office without having been laid open to public inspection, the furnishing of a sample shall only be effected to an expert in the art.

European Patent

In respect of those designations in which a European Patent is sought a sample of the deposited microorganism will be made available until the publication of the mention of the grant of the European patent or until the date on which the application has been refused or withdrawn or is deemed to be withdrawn, only by the issue of such a sample to an expert nominated by the person requesting the sample (Rule 28(4) EPC).

Finland

The applicant hereby requests that, until the application has been laid open to public inspection (by the National Board of Patents and Registration), or has been finally decided upon by the National Board of Patents and Registration without having been laid open to public inspection, the furnishing of a sample shall only be effected to an expert in the art.

France

The applicant hereby requests that, until the publication of the grant of the patent, the withdrawal or refusal of the application, the deposited culture shall only be accessible to an expert designated by the applicant.

Iceland

The applicant hereby requests that, until a patent has been granted or a final decision taken by the Icelandic Patent Office concerning the application which has not resulted in a patent, the furnishing of a sample shall only be effected to an expert in the art.

Ireland

The applicant hereby requests that, until the preparations for publication of the patent application have been completed by the Comptroller, a sample of the microorganism should be made available only to an expert.

Netherlands

The applicant hereby requests that until the date of grant of a patent or date on which the application is refused or withdrawn or lapsed, the microorganism shall be made available as provided in Rule 31F(1) of the Patent Rules only by issue of a sample to an expert.

Norway

The applicant hereby requests that, until the application has been laid open to public inspection (by the Norwegian Patent Office), or has been finally decided upon by the Norwegian Patent Office without having been laid open to public inspection, the furnishing of a sample shall only be effected to an expert in the art.

Singapore

The applicant hereby requests that the furnishing of a sample of a microorganism shall only be made available to an expert.

Spain

The applicant hereby requests that until the date of grant of a patent or date on which the application is refused or withdrawn or lapsed, the biological material shall be made available as provided in Article 45 SPL only by issue of a sample to an expert.

Sweden

The applicant hereby requests that, until the application has been laid open for public inspection (by the Swedish Patent Office), or has been finally decided upon by the Swedish Patent Office without having been laid open to public inspection, the furnishing of a sample shall only be effected to an expert in the art.

United Kingdom

The applicant hereby requests that the furnishing of a sample of a microorganism shall only be made available to an expert.

Other Nominated Designations

Where such provisions exist, the applicant hereby requests that, until the publication or grant of a patent, the withdrawal or refusal of the application, the deposited culture shall only be effected to an expert in the art.

What we claim is:

1. An isolated or biologically pure culture of a Chloroflexi-like microorganism designated T81 on deposit at Deutsche Sammlung von Mikroorganismen and Zellkulturen GmbH, Mascheroder Weg 1b, D-38124, Braunschweig, Germany, Accession No. DSM 21103.

2. An isolated culture of an aerobic cellulose degrading thermophilic Chloroflexi-like microorganism comprising a 16S ribosomal subunit nucleic acid sequence selected from the group consisting of:
  (a) SEQ ID NO:1;
  (b) a variant nucleic acid sequence that has greater than 95% identity to a nucleic acid sequence of (a);
  (c) a nucleic acid sequence fully complementary to the nucleic acid of (a);
  (d) a sequence of at least 100 contiguous nucleotides in length, capable of hybridizing to the sequence of any one of (a) to (c) under stringent hybridization conditions, wherein the stringent hybridization conditions are pre-washing in solution of 6×SSC, 0.2% SDS; hybridizing at 65° C.; 6×SSC, 0.2% SDS overnight; followed by two washes of 30 minutes each in 1×SCSC, 0.1% SDS at 65° C.; and
  (e) a fragment of (a) comprising at least 100 contiguous nucleotides.

3. A microorganism according to claim 2, wherein the variant nucleic acid sequence has at least 96%, 97%, 98%, or 99% identity to a nucleic acid sequence of any one of (a) to (e).

4. A cellulose degrading composition comprising one or more microorganisms according to any one of claims 1 to 3 and a carrier or diluent.

5. A method of degrading a cellulose containing material which method comprises treating the material with one or more microorganisms according to any one of claims 1 to 3.

6. The method of claim 5 wherein the cellulose containing material is waste cellulose, wood, crops, grasses, sewage, forestry pulp, wood chip pulp, paper, cardboard, cellulose fines, or combinations thereof.

7. The method of claim 5 wherein the treatment is effected at a temperature of from about 40° C. to 75° C.

8. The method of claim 7 wherein the temperature is from about 60° C. to 70° C.

9. The method of claim 7 wherein the temperature is about 60-65° C.

10. The method of claim 5 wherein the treatment is effected at a pH of about 3.0 to 7.5, or 4.0 to 7.0.

11. The method of claim 10 wherein the pH is 5.0.

12. The method of claim 5 which is an aerobic treatment method.

* * * * *

SEQUENCE LISTING

```
<160> NUMBER OF SEQ ID NOS: 13

<210> SEQ ID NO 1
<211> LENGTH: 1392
<212> TYPE: RNA
<213> ORGANISM: Chloroflexi T81

<400> SEQUENCE: 1
augcaagucg aacgcucucu ccgcgagggg agggaguggc ggacgggugga ggaacacgug      60 ggugaccugc ccugcagugg gggauaccgg ugcgaaagug ccgacaaucc cgcauacggu     120
ggcgucuugc gagaggcgcc aggaaagcuu ccugccggag ggugggaggc gcugcaggag     180
gggccugcgc ccgauuagcu gguugguagg guaaaggccu accaaggcga cgaucggugu     240
cuggucugag aggacgauca gccacacugg gauugagaga cggcccagac uccuacgggg     300
ggcagcagug agggaucuuc ggcaaugggc gaaagccuga ccgagcgacg ccgcgugcag     360
gaagaaggcc uucgguugu aaacugcuuu ucuggggga gagagaggac gguacccccag     420 gaagaagccc cggcaaacua cgugccagca gccgcgguaa gacguagggg gcgagcguug     480
uccggaguua cugggcguaa agggccugua ggcggucggg cagguuccgg cggacagccc     540
gcggcuucac ugcgggagca gcaggaagac ggcucgacuu gagggccaca gagggacaug     600
gaauucccgg uggagcggug aaaugcguag agaucgggaa gaacaccgaa ggcgaaggca     660
guguccuggg ugguaccuga cgcugagagg cgaaagcuag gggagcgaac gggauuagau     720 accccggguag uccuagccgu aaacgcugac cacuaggugu gugggagau cgacccccug     780 cgcgccgaag cgaacgcaug aagugguccg ccuggggagu acgccgcaa ggcuaaaacu     840 caaaggaauu gacggggacc cgcacaagca gcggagcgug ugguuaauu cgaugcaacg     900 cgaagaaccu uaccaggguu ggacaugcgc gcugaggguc cagagauggg ccggcccgca     960
agggaggcgc gcacaggugc ugcauggcug ucgucagcuc gugccgugag guguugggguu    1020 aagucccgca acgagcgcaa cccucgcucu cgguuggaug uguccgaggg gacugccgcg    1080
cacaacgcgg aggaaggugg ggaugacguc aagucagcau ggcccugaca uccugggcga    1140
cacacacgcu acaauggucg ggacagcggg cagcgacccg cgacgggga gccaaucccu    1200 caaacccgau cucagugcag auugcaggcu gcaacccgcc ugcaugaagg aggaguugcu    1260
aguaaccgcc ggucagcaca cggcggugaa uacguucucg ggucuuguac acaccgcccg    1320
ucacaccacg aaagccggca acaccugaag ccgcugggcg aaccccucgu gagaggggag    1380
gcaggcgucg ag                                                        1392

<210> SEQ ID NO 2
<211> LENGTH: 1392
<212> TYPE: RNA
<213> ORGANISM: Chloroflexi T26

<400> SEQUENCE: 2
```

```
augcaagucg aacgcucucu ccgcgagggg agggagaggc ggacgggaga ggaacacgug      60
ggugaccugc ccugcagugg gggauaccgg ggcgaaagcg ccgacaaucc cgcauacggu     120
ggcgucuugc gagaggcgcc aggaaagcuu ccugccggag ggugggaggc gcugcaggag     180
gggccugcgc ccgauuagcu aguuggaugg guaauggccu accaaggcga cgaucgguag     240
cuggucugag aggacgauca gccacacugg gauugagaga cggcccagac uccuacgggg     300
ggcagcagug agggaucuuc ggcaaugggu gaaagccuga ccgagcgacg ccgcgugcag     360
gaagaaggcc uucggguugu aaacugcuuu ucuggggaa gagggaggac gguacccag     420
gaagaagccc cggcaaacua cgugccagca gccgcgguaa gacguagggg gcgagcguug     480
uccggaguua cugggcguaa agggccugua ggcggucggg cagguuccgg cggacagccc     540
gcggcuucac ugcgggagaa gcaggaagac gguccgacuu gagggccaca gagggacaug     600
gaauucccgg uggagcggug aaaugcguag agaucgggaa gaacaccgaa ggcgaaggca     660
guguccuggg gguaccccuga cgcugagagg cgaaagcuag gggagcgaac gggauuagau     720
accccgguag uccuagccgu aaacgcugac cacuaguguu gggggagau cgaccccccug     780
cgcgccgaag cgaacgcaug aagugguccg ccuggggagu acggccgcaa ggcuaaaacu     840
caaaggaauu gacgggggacc cgcacaagca gcggagcgug ugguuuaauu cgaugcaacg     900
cgaagaaccu uaccaggguu ggacaugcac gcugaggguc cagagauggg ccggcccgca     960
agggaggcgu gcacaggugc ugcauggcug ucgucagcuc gugccgugag uguugggguu    1020
aagucccgca acgagcgcaa cccucgcucu cgguuggaaau uauccgaggg gacugccgcg    1080
cacaacgcgg aggaaggugg ggaugacguc aagucagcau ggcccugaca uccugggcga    1140
cacacacgcu acaauggucg ggacagcggg cagcgacccg cgacgggga gccaauccccu    1200
uaaacccgau cucagugcag auugcaggcu gcaacccgcc ugcaugaagg aggaguugcu    1260
aguaaccgcc ggucagcaca cggcggugaa uacguucucg ggucuuguac acaccgcccg    1320
ucacaccacg aaagccggca acaccugaag ccgcugggcg aaccccucgu cggagggag    1380
gcaggcgucg ag                                                        1392

<210> SEQ ID NO 3
<211> LENGTH: 1392
<212> TYPE: RNA
<213> ORGANISM: Chloroflexi T12

<400> SEQUENCE: 3
augcaagucg aacgcucucu ccgcgagggg agggagaggc ggacgggaga ggaacacgug      60
ggugaccugc ccugcagugg gggauaccgg ggcgaaagcg ccgacaaucc cgcauacggu     120
ggcgucuugc gagaggcgcc aggaaagcuu ycygccggag ggcgggaggc gcugcaggag     180
gggccugcgc ccgauuagcu aguuggaugg guaauggccu accaaggcga cgaucgguag     240
cuggucugag aggacgauca gccacacugg gauugagaga cggcccagac uccuacgggg     300
ggcagcagug agggaucuuc ggcaaugggc gaaagccuga ccgagcgacg ccgcgugcag     360
gaagaaggcc uucggguugu aaacugcuuu ucuggggaa gagggaggac gguacccag     420
gaagaagccc cggcaaacua cgugccagca gccgcgguaa gacguagggg gcgagcguug     480
uccggaguua cugggcguaa agggccugua ggcggucggg cagguuccgg cggacagccc     540
gcggcuucac ugcgggagaa gcaggaagac gguccgacuu gagggccaca gagggasaug     600
gaauucccgg uggagcggug aaaugcguag agaucgggaa gaacaccgaa ggcgaaggca     660
guguccuggg gguaccccuga cgcugagagg cgaaagcuag gggagcgaac gggauuagau     720
```

-continued

| | |
|---|---|
| accccgguag uccuagccgu aaacgcugac cacuaggugu gugggagau cgaccccug | 780 |
| cgcgccgaag cgaacgcaug aaguggaccg ccuggggagu acggccgcaa ggcuaaaacu | 840 |
| caaaggaauu gacggggacc cgcacaagca gcggagcgug ugguuuaauu cgaugcaacg | 900 |
| cgaagaaccu uaccagggu ggacaugcac gcugagggu cagagauggg ccggcccgca | 960 |
| agggaggcgu gcacaggugc ugcauggcug ucgucagcuc ugccgugag uguugggu | 1020 |
| aagucccgca acgagcgcaa cccucgcucu cgguuggagc uauccgaggg gacuccgcg | 1080 |
| cacaacgcgg aggaaggugg ggaugacguc aagucagcau ggcccugaca uccugggcga | 1140 |
| cacacacgcu acaauggucg ggacagcggg cagcgacccg cgacgggga gccaauccu | 1200 |
| yaaacccgau cucagugcag auugcaggcu gcaacccgcc ugcaugaagg aggaguugcu | 1260 |
| aguaaccgcc ggucagcaca cggcggugaa uacguucucg ggucuuguac acaccgcccg | 1320 |
| ucacaccacg aaagcgggca acaccugaag ccgcugggcg aaccccucgu cggaggggag | 1380 |
| gcaggcgucg ag | 1392 |

<210> SEQ ID NO 4
<211> LENGTH: 1386
<212> TYPE: RNA
<213> ORGANISM: Ktedonobacter racemifer

<400> SEQUENCE: 4

| | |
|---|---|
| acgcuggcgg cgugccuaac acaugcaagu cgaacgcccu cucgcaagag agggagugc | 60 |
| ggacggugga guaacacaug gguaccugcc ccgaggugag gaauaccggc gagaaaucgc | 120 |
| cgacaauacc gcauauguuc cuccgggaac aaagcucgca agggcgccuu gggaugggcc | 180 |
| uguggccgau uagcuuguug gugaggugaa agcucaccaa ggccacgauc gguagcuggu | 240 |
| cugagaggau ggucagccac acugggauug agaacggccc agacuccuac ggggggcagc | 300 |
| agugaggaau uuucgucaau gggggcaacc cugaacgagc aacgccgcgu gcaggaggac | 360 |
| gcuuuucgga guguaaacug cuuuucuugg ggacgaguaa ggacgguacc yaaggaauaa | 420 |
| gccccggcua acuacgugcc agcagccgcg guaauacgua ggggcaagc guuguccgga | 480 |
| guuauugggc guaaagcgca cgcaggcggu uucguacguc cggagugaca guucccggcu | 540 |
| caacugggaa aggucuucgg aaacggcgag acuugagggc uucagaggga cacggaauuc | 600 |
| cggguggagu ggugaaaugc guagagaucc ggaggaacac caauggcgaa ggcaguguc | 660 |
| ugggaagcau cugacgcuca ggugcgaaag cuaggggagc gaacaggauu agauacccug | 720 |
| guaguccuag ccguaaacga ugaccacuag gugugggagg uaucgacccc uuccgugccg | 780 |
| ucgcaaacgc aguaaguggu ccgccugggg aguacggucg caagauuaaa acucaaagga | 840 |
| auugacgggg acccgcacaa gcagcggagc guguggua auucgaugca acgcgaagaa | 900 |
| ccuuaccaag ucuugacaug cagaugcacc agcgguaaug cgcugcccu cggggcguu | 960 |
| ugcacaggug cugcauggcu gucgucagcu cgugucguga gaugugggu uaagucccgc | 1020 |
| aacgagcgca accccuacug ccauuacaa cuucuaggcg gaacugcccu cacggaggag | 1080 |
| aggcgggau gacgucaagu cagcacggcc cuuacgacuu gggcgacaca cacgcuacaa | 1140 |
| uggccagyaa caaagggaug ccaacccgcg aggggagcc aagcucaaaa accuggucuc | 1200 |
| aguucagauu gcaggcugaa acucgccugc augaaggugg aguugcuagu aaccguaggu | 1260 |
| cagcacacua cggugaauac guucccgggu cuuguacaca ccgcccguca caccgaaaa | 1320 |
| gucggcaaca ccugaagccg ccaggcuaac ucuucggaga ggcaggcguc gagggugggg | 1380 |
| uugggug | 1386 |

```
<210> SEQ ID NO 5
<211> LENGTH: 1472
<212> TYPE: RNA
<213> ORGANISM: Herpetosiphon aurantiacus

<400> SEQUENCE: 5
gaguuugauc cuggcucagg acgaacgcug gcggcgugcc uaaugcaugc aagucgaacg      60
cauucuucgg aaugaguggc gcacggcuga ggaacacgug acuaaccuac cccggugugg     120
gggauaacgg gucgaaagac ucgcuaaucc cgcauacgau ccgccucggc ggaggaaagc     180
cgcaaggcgc acugggcggg ggucgcgucc cauuagauag uugguguggu aauggcgcac     240
caagucgaug augggucucu ggucugagag gacgaccaga cagauuggga cugagacacg     300
gcccaaacuc cuacgggggg cagcagcaag gaauuuucgg caaugggcgc aagccugacc     360
gagcaacgcc gcguggagga ugacggcucu uggguuguaa acuccuuuug gggggacga     420 uaaugacggu acccuccgaa ucaggcccgg cuaacuacgu gccagcagcc gcgguaauac     480
guaggggcca agcguugucc ggaauuacug ggcguaaagc gugguaggu ggucgaugau     540 gugccgcgug aaagccgcgg aguaaugccg gcgaggucgc gguagacacg uugacuagag     600
gcucgcagag gaacguggaa uucccggugu aguggugaaa ugcguagaua ucggaggaa     660 caccagggc gcaagcggcg uucgggcga gaccugacac ugagccacga cggcgugggg     720
agcaaacagg auuagauacc cugguagucc acgcaguaaa cgaugcauac caggugugg     780 auggcguucg cgucguuccg ugccgcagcu uacgcgauga uaugccgcc uggggacuac     840 gagcgcaagc uuaaaacuca aaggaauuga cggggggccg cacaagcagc ggagcgugug     900
guuuaauucg acgcaacgcg aagaaccuua ccuagucuug acauagcacu gcaagcuucg     960
gaaaugaagu cgccuucgag ggugugcuac aggugcugca uggcugucgu cagcucugu     1020 cgugagaugu ugggguuaagu cccgcaacga gcgcaacccc ugugaggugu acaaguguc     1080 accucagacu gccguuguca acaacggagg aaggcgggga ugacgucaag uccgcauggc     1140
ccuuacgacu agggcgacac acacgcuaca auggcuggga gaaugcgccg cgaccuggca    1200
acaggcagcg aaucgagaac accagucaca guucagauug ggggcugcaa cucgccccca    1260
ugaaggcgga guucuaagua aucgccgguc agccauacgg cggugaauca guacccgggc    1320
cuuguacaca ccgcccguca cgucaaugga ugggggaaaca ccugaaguc gugggcuaac    1380 cgcaaggagg cagcggccga ggguggggcu cguaacuggg acgaagucgu aacaagguag    1440
ccguaccgga aggugugggcu ggaucaccuc cu                                1472

<210> SEQ ID NO 6
<211> LENGTH: 1479
<212> TYPE: RNA
<213> ORGANISM: Chloroflexus aggregans

<400> SEQUENCE: 6
agaguuugau ccuggcucag gacgaacgcu ggcggcgugc cuaaugcaug caagucgaac      60
gcagcggcca agugccggcu gcguggcgaa cggcugagga acacguggu caccaccccc     120 ggaguggggg auaccccguc gaaagacggg acaaucccgc auacgcucua cggaggaaag     180
ccauacggcg cuccgggacg ggccugcggc ccaucaggua guggugugg uaacggcgca     240 ccaagccacu gacggguacc cggucugaga ggacggccgg gcagacuggg acugcgacac     300
ggcccagacu ccuacgggag gcagcagcaa ggaauuuucc ccaaugggca cgccugag     360 ggagcaacgc cgcguggagg acgacggccu ucggguugua aacuccuuuc gggugggacg    420
```

```
agacugacgg uaccaccaga agcagccccg cuaacucug ugccagcagc cgcgguaaga    480
cagaggggc aagcguuguc cggaguuacu gggcguaaag ggcgcggagg cggucugcug    540
cgucggcgcu gaaagcgccc cgcuuaacgg ggcgaggcgc gccgauacga gcaggcugga    600
ggcgagcaga gggugguggua auuccggugu gagcggugaa augcguagau auccggagga    660
acgccggugg agcagucggc caccugggcu cgaccugacg cugcggcgcg accgcguggg    720
gagcaaaccg gauuagauac ccggguaguc cacgccguaa acgaugccgg cucggcguuu    780
ggcgcgcgug agcgucugg gugccuuagc uaacgcggua agccggccgc cuggggacua    840
cgagcgcaag cuuaaaacuc aaaggaauug acggggcccc gcacaagcag cggagcgugu    900
gguuaauuc gacgcaaccc gaagaaccuu acccgggcuu gacaugacgc ugcaggcgcg    960
ggaaaccgcg cggccuuuga ggguggcuca caggugcugc auggcugucg ucagcucgug   1020
ucgugagaug uugggguucag ucccgcaacg agcgcaaccc gcgucgguag uuaccgguu   1080
cuaccgagac ugccgccgag accggcggag aaggcgcgg augacgucaa gucagcaugg   1140
cccugacguc cggggcgaca cacacgcuac aauggccacg acaaugcguu gccacgccgc   1200
aaggcggcgc uaaucgccaa acguggcucu agucagauc ggggcugca acucgccccc   1260
gugaaggcgg aguugcuagu aaccgcguau cagccauggc gcggugaaua cguucccggg   1320
ccuuguacac accgcccguc acgucauggg aguggcuaau gcuugaaguc cgugugcuaa   1380
ccccccacgg ggaggcagcg gccgagggca ggagccgcga cugggacgaa gucguaacaa   1440
gguagccgua ccggaaggug cggcuggauc accuccuuu                          1479
```

<210> SEQ ID NO 7
<211> LENGTH: 1469
<212> TYPE: RNA
<213> ORGANISM: Roseiflexus castenholzii

<400> SEQUENCE: 7

```
agaguuugau ccuggcucag gacgaacgcu ggcggcgugc cuaaugcaug caagucgaac    60
gcacgcgcuu cggcgcguga guggcgcacg gcugaguaac acguggaac ccgcccuccg    120
gugggggaua acgagacgaa agucgcgcua auccgcauga cguccgcaag gggaaagcgc    180
uucggcgcgc cggaggaggg gccugcggcc caucaggugg uuggugggu aacggccuac    240
caagccgaug acgggguagcu ggucuggag gaugaccagc cagacuggga cugagacacg    300
gcccagacuc cuacgggagg cagcagcaag gaauuuucgg caaugggcgc aagccugacc    360
gagcaacgcc gcgugcggga ugacggccuu cgggguguaa accgcuuuc gggggacga    420
cuacgacggu acccccggaa gaagccccgg cuaacucugu gccagcagcc gcgguaagac    480
agaggggcag cguugucc ggaguuacug gcguaaagc gcgcagggc gguggucuca    540
gugucgugug aaagccccg gcucaaccgg ggaggucau ggcaaacuag acgacuagag    600
cggcggagag gccccucgaa uugccggugu agcggugaaa ugcguagaga ucggcaggaa    660
gaccaagggg gaagccaggg ggcuggccgc ugcugacgc ugaggcgcga cagcgugggg    720
agcaaaccgg auuagauacc cggguagucc acgccguaaa cgaugaccac ucggcgugug    780
gcgacuauug acgucgcggc gcgccuaagc uuacgcguga aguggccgc cugaacua    840
cgagcgcaag cuuaaaacuc aaaggaauug acggggcccc gcacaagcag cggagcgugu    900
gguuaauuc gacgcaaccc gaagaaccuu acccaggcug gacaugacgg ugcaggcggc    960
ggaaacgucg cggccuucga ggggaccguca caggugcugc auggcugucg ucagcucgug   1020
ucgugagaug uuggguuaag ucccgcaacg agcgcaaccc cugcgguag uuaccgguu    1080
```

```
cuaaccggac ugcccuucgg ggaggaaggc ggggaugacg ucaaguccgc auggcccuga      1140
cgccuggggc gacacacacg cuacaauggc gccgacaaug cguggcgacc gcgcgagcgg      1200
aggcaaaucg ccaaacggcg ucucagugca gaucggggc ugcaacucgc ccccgugaag       1260
gcggaguugc uaguaaccgc guaucagcca uggcgcggug aauacguacc cgggccuugu      1320
acacaccgcc cgucacguca ugggaguugu caaugccuga aguccgugcg cuaaccguca      1380
ggaggcagcg gccgagggca ggggcagcga cuggacgaa gucguaacaa gguagccgua       1440
ccggaaggug cggcuggauc accuccuuu                                        1469

<210> SEQ ID NO 8
<211> LENGTH: 1500
<212> TYPE: RNA
<213> ORGANISM: Sphaerobacter thermophilus

<400> SEQUENCE: 8
ggcggcgugc cuaaugcaug caagucguac gggagccgcu uuggcggucg accguggcgg        60
acgggugagg aacacguggg uaaccugccc cggcgcgggg gauaaccgcg ggaaaccgug       120
gcuaauaccc caugggcucg guuggggug accugaucga gcaaaggcgg aagccgugcc        180
gggaggggcc ugcggccuau cagcuagacg gugggguaau ggccuaccgu ggcgaugacg       240
gguagcuggu cugagaggac gaucagccac acggggacug agacacgccc cgacuccua        300 cgggaggcag cagcaaggaa uuuccgcaa ugggcgcaag ccugacggag cgacgccgcg        360
uggaggauga cgcccuucgg gguguaaacu ccuuuucggg gggacgaagg cagugacggu       420
acccccggaa gaagcaccgg cuaacuacgu gccagcagcc gcgguaagac guagggugcg      480
agcguugucc ggaguuacug ggcguaaagg gcgcguaggc ggcugccgc gucgcacgug        540 aaagccccg gcucaaccgg ggaggucgu gcgagacggg guggcuagag gcaggagag         600 gcuggugaa uucccggugu agcggugaaa ugcguagaga ucggaggaa caccgguggc       660 gaaggcggcc agcuggcccu gaccugacgc ugaggcgcga aggcgcgggg agcgaacggg      720
auuagauacc ccgguagucc gcgcaguaaa cgcugugggac uaggugugg aggugu ugac     780 cccuuccgug ccggcgcuaa cgcaguaagu ccaccgccug gggaguacgg ccgcaaggcu      840
aaaacucaaa ggaauugacg ggggcccgca caagcagcgg agcguguggu uuaauucgac      900
gcaacgcgca gaaccuuacc agggcuugac auccccggaa ccccuggaa accgggggug       960 cccuucgggg agccgggaga caggugcugc auggcugucg ucagcucgug ucgugagaug     1020
uuggguuaag ucccgcaacg agcgcaaccc ucguggcuag uuacgguggu guuuagccag     1080
acugccgggc acaacccgga ggaagggggg gaugacguca aguccgcaug gcccugacgc     1140 ccuggcgac acacacgcua caauggccgg gacagcgggc ggccaagcgg caacgcggag      1200
ccaaucccuc aaaccgguc ucaguucgga uuggggcug caacucgccc ccaugaaggc       1260
ggaguugcua guaaccgcag gucagccaua cugcggugaa uauguucccg ggccuuguac    1320
acaccgcccg ucacgucacg aaagccggca caccugaag ccgguggcc aacccgauac      1380 gggaggcagc cgucgaaggu ggggcuggug auugggacga agucguaaca agguagccgu     1440
agcggaagcu ggggcuggug auugggacga agucguaaca agguagccgu agcggaagcu     1500

<210> SEQ ID NO 9
<211> LENGTH: 1472
<212> TYPE: RNA
<213> ORGANISM: Dehalococcoides sp. BHI80-52

<400> SEQUENCE: 9
```

| | |
|---|---:|
| agaguuugau cauggcucag gaugaacguu ggcggcgugc cuaacacaug caagucgaac | 60 |
| gagcagccgg auucuucgga aaccgguggg cgaguggcga acgggugagu aacacgugga | 120 |
| uaaucugccc cgaagcgggg gauaacugcu ggaaacggca gcuauaccg caugugcuug | 180 |
| ccggaucgga uggucgggua aguaaagcuu ggcgcuucg ggaggagucc gcggccgauu | 240 |
| agcuaguugg cgagguaaug cucaccaag gcgaugaucg uagggggcg ugagagcgug | 300 |
| accccccaca cuggaacuga gacacggucc ugacccuac gggaggcagc agugaggaau | 360 |
| auugcacaau gggcgaaagc cugaugcagc aacgccgcgu gggggaugaa ggccuucggg | 420 |
| uuguaaaccc ccuuucgcg ggaagagaaa ggacgguacc gcaggaauaa gucucggcua | 480 |
| acuacgugcc agcagccgcg guaaaacgua ggaggccaac guuauccgga uuuacuuggg | 540 |
| cguaaagcgc ucgcaggcgg cuucguaagu cugaugugaa agcccccggc uuaacugggg | 600 |
| gaggccauug gauacugcgg agcuugagga caggagagga aaguggaauu cccgguguag | 660 |
| cgguggaaug cguagauauc gggaggaacu ccaguggcga aggcgacuuu cuggccuguu | 720 |
| ccugacgcuc aggagcgaaa gcguggguag cgaacaggau uagauacccu gguaguccac | 780 |
| gcuguaaacg augugaacua gguguuggcg cguuuauggc gucagugccg agcuaacgc | 840 |
| guuaaguuca ccgccugggg acuacggccg caaggcuaaa acucaaagga auugacgggg | 900 |
| gcccgcacaa gcagcggagc gugugguuua auucgaugca acgcgaagag ccuuaccugg | 960 |
| guuugacaug uacguaguag gaagccgaaa ggcgacccac cccucgggga gcguacacag | 1020 |
| gugcugcaug gcugucguca gcucgugccg ugagguguug gguuaagucc cgcaacgagc | 1080 |
| gcaaccccug uugcuaguua caugugcua gcgagacugc cgguuuaacg ccggaggaag | 1140 |
| gaggggauga cgucaaguca gcauggccuu uauguccagg gcuacacaca cgcuacaaug | 1200 |
| gccgguacaa cggguagcca agucgcgaga uggagcuaau cccaucaaag ccggucucag | 1260 |
| uucggauugc aggcugcaac ucgccugcau gaagucggag uugcuaguaa ccgcguguca | 1320 |
| gcaauagcgc ggugaauacg uucccgggcc uuguacacac cgcccgucac gucauggag | 1380 |
| ccgguaacac cugaagucgg cuggccaacc ugcaagggag gcggcugccu agggugggac | 1440 |
| ugguaacugg gacgaagucg uaacaaggua ac | 1472 |

<210> SEQ ID NO 10
<211> LENGTH: 1431
<212> TYPE: RNA
<213> ORGANISM: Chloroflexi bacterium Ellin7237

<400> SEQUENCE: 10

| | |
|---|---:|
| gacaaacgcu ggcggcgugc cuaacacaug caagucgaac ggggcauagu uuucggauua | 60 |
| ugccgagugg cggacgggug aguaagacgu gggcgaccua ccgcuuggag ggggauaccc | 120 |
| cgcggaaacg cgggauaaga ccgcauacgc ugaucgggu agauccggau caggaaaacg | 180 |
| cgagagcgug ccaagugagg ggccugcggc cgauuagcua guuggggggg uaacggccuc | 240 |
| ccaaggcgac gaucgguagc uggucugaga ggacgaucag ccacacuggg auugagaacg | 300 |
| gcccagacuc cuacgggggg cagcagugag ggaucuucgg caauggggga aacccugacc | 360 |
| gagcgacgcc gcgugcggga cgaaggccuu cgggucguaa accgcuuuuc uugggacga | 420 |
| gaauggacgu uacccgagga agaagccucg gcuaacuacg ugccagcagc cgcgguaaua | 480 |
| cguaggaggc gagcguuguc cggaguuacu gggcguaaag ggugcguagg cggcugcgcg | 540 |
| cguggagggu gaaaucucuc ggcuuacccg gagggggcu uccagacgg cguggccuuga | 600 |
| gggacggaga ggggcgugga auuccggugu gagcggugaa augcguagag auccggagga | 660 |

-continued

```
acaccgacgg cguaggcagc gcccuggccg uuuccugacg cugaagcacg aaagcugggg      720
gagcaaacag gauuagauac ccugguaguc cagcccuaa  acgaugucca ccggguggccg     780 ggggguaucga ccccucggu  gccgaagcua acgugaugag uggaccgccu ggggaguacg     840
gccgcaaggu ugaaacucaa aggaauugac ggggcccgc  acaagcagcg gagcgugugg     900
uuuaauucga ugcgacgcga agaaccuuac cugggcuuga caugugauug caccaggggu     960
aaugcccugu ccucgcaaga gagcggcuac acaggugcug cauggcuguc gucagcucgu    1020
gccgugaggu guuggguuaa uccccuaac  gagcgcaacc ccugggggucc guuaccaugg   1080 ugugucgggc ccgacugccg cgcgcaacg  ggaggaaggc ggggaugacg ucaagucagc    1140
acggcccuga cguccagggc gacacacacg cuacaauggc cgauacaacg ggucgcgaag    1200
ccgcgaggcg gagccaaucc caccaaaguc ggcucucaguu cggaucguag gcugaaaccc   1260
gccugcguga agccggaguu gcuaguaacc gcggucagc  acaccgcggu gaauacguuc    1320
ccgggccuug uacaccgcc  ccgucacacc acgaaagccg ggacaccug  aagccgcugg    1380 gcaaacucuu cggagaggca ggcgucgagg guggaaucgg ugauuggggu g              1431
```

<210> SEQ ID NO 11
<211> LENGTH: 1375
<212> TYPE: RNA
<213> ORGANISM: Chloroflexi T26

<400> SEQUENCE: 11

```
acgcucucuc cgcgagggga gggaguggcg gacgggugag gaacacgugg gugaccugcc      60 cugcagugg  ggauaccggg gcgaaagcgc cgacaauccc gcauacggug gcgucuugcg    120
agaggcgcca ggaaagcuuc cugccggagg gugggaggcg cugcaggagg ggccugcgcc    180
cgauuagcua guuggugaggg uaauggccua ccaaggcgac gaucgguagc uggucugaga    240
ggacgaucag ccacacuggg auugagagac ggcccagacu ccuacggggg gcagcaguga    300
gggaucuucg gcaaugggug aaagccugac cgagcgacgc cgcgugcagg aagaaggccu    360 ucggguuguga acugcuuuuu cugggggaag agggaggacg guaccccagg aagaagcccc    420
ggcaaacuac gugccagcag ccgcgguaag acguaggggg cgagcguugu ccggaguuac    480
ugggcguaaa gggccuguag gcggucgggc agguuccggc ggacagcccg cggcuucacu    540
gcgggagaag caggaagacg guccgacuug agggccacag agggacaugg aauucccggu    600
ggagcgguga aaugcguaga gaucgggaag aacaccgaag gcgaaggcag uguccugggu    660
gguaccugac gcugagaggc gaaagcuagg ggagcgaacg ggauuagaua cccccgguagu    720 ccuagccgua aacgcugacc acuaggugug ggggagauc  gaccccccugc gcgccgaagc    780 gaacgcauga aguggucccgc cugggagua  cggccgcaag gcuaaaacuc aaaggaauug    840
acggggaccc gcacaagcag cggagcgugu gguuaauuc  gaugcaacgc gaagaaccuu    900
accaggguug gacaugcacg cugagggucc agagaugggc cggcccgcaa gggaggcgug    960
cacaggugcu gcauggcugu cgucagcucg ugccgugagg uguuggguua aguccccgcaa   1020 cgagcgcaac cccucgcucuc gguuggaauu auccgagggg acugccgcgc acaacgcgga   1080 ggaaggugg  gaugacguca agucagcaug gcccugacau ccugggcgac acacacgcua    1140
caauggucgg gacagcgggc agcgaccgg  cgacggggga ccaauccccuu aaacccgauc    1200 ucagugcaga uugcaggcug caacccgccu gcaugaagga ggaguugcua guaaccgccg    1260
gucagcacac ggcggugaau acguucucgg gucuuugcaca caccgcccgu cacaccacga    1320
aagccggcaa caccugaagc cgcugggcga acccccucguc ggaggggagg caggc         1375
```

<210> SEQ ID NO 12
<211> LENGTH: 1386
<212> TYPE: RNA
<213> ORGANISM: Chloroflexi T12

<400> SEQUENCE: 12

```
caugcaaguc gaacgcucuc uccgcgaggg gagggagugg cggacgggug aggaacacgu      60
ggugaccug cccugcagug gggauaccg gggcgaaagc gccgacaauc cgcauacgg       120
uggcgucuug cgagaggcgc caggaaagcu uycygccgga gggcgggagg cgcugcagga    180
ggggccugcg cccgauuagc uaguuggaug gguaauggcc uaccaaggcg acgaucggua    240
gcuggucuga gaggacgauc agccacacug ggauugagag acgcccaga cuccuacggg     300
gggcagcagu gagggaucuu cggcaauggg cgaaagccug accgagcgac gccgcgugca    360
ggaagaaggc cuucggguug uaaacugcuu uucugggga agagggagga cgguacccca     420
ggaagaagcc ccggcaaacu acgugccagc agccgcggua agacguaggg ggcgagcguu    480
guccggaguu acugggcgua aagggccugu aggcggucgg gcagguuccg gcggacagcc    540
cgcggcuuca cugcgggaga agcaggaaga cgguccgacu ugagggccac agagggasau    600
ggaauucccg guggagcggu gaaaugcgua gagaucggga agaacaccga aggcgaaggc    660
aguguccugg ggguaccug acgcugagag gcgaaagcua ggggagcgaa cgggauuaga    720
uaccccggua guccuagccg uaaacgcuga ccacuagggug uguggggaga ucgacccccu    780
gcgcgccgaa gcgaacgcau gaagugguucc gccuggggag uacggccgca aggcuaaaac    840
ucaaaggaau ugacggggac ccgcacaagc agcggagcgu gugguuuaau ucgaugcaac    900
gcgaagaacc uuaccagggu uggacaugca cgcugagggu ccagagaugg gccggcccgc    960
aagggaggcg ugcacaggug cugcauggcu gucgucagcu cgugccguga ggguguuggu   1020
uaagucccgc aacgagcgca acccucgcuc ucgguuggag cuauccgagg gacugccgc    1080
gcacaacgcg gaggaaggug gggaugacgu caagucagca uggcccugac auccugggcg   1140
acacacacgc uacaauggauc gggacagcgg gcagcgaccc ggcgacgggg agccaauccc   1200
uyaaacccga ucucagugca gauugcaggc ugcaacccgc cugcaugaag gaggaguugc   1260
uaguaaccgc cggucagcac acggcgguga auacguucuc gggucuugua cacaccgccc   1320
gucacaccac gaaagcgggc aacaccugaa gccgcugggc gaaccccucg ucggagggga   1380
ggcagg                                                              1386
```

<210> SEQ ID NO 13
<211> LENGTH: 1386
<212> TYPE: RNA
<213> ORGANISM: Chloroflexi T81

<400> SEQUENCE: 13

```
agucgaacgc ucucuccgcg aggggaggga guggcggacg ggugaggaac acgugggguga    60
ccugcccugc aguggggau accggugcga aagugccgac aauccccgcau acgguggcgu   120
cuugcgagag cgccaggaa agcuuccugc cggagggugg gaggcgcugc aggaggggcc    180
ugcgcccgau uagcugguug guagggguaaa ggccuaccaa ggcgacgauc gguagcuggu   240
cugagaggac gaucagccac acugggauug agacggcc cagacuccua cgggggcag     300
cagugaggga ucuucggcaa ugggcgaaag ccugaccgag cgacgccgcg ugcaggaaga   360
aggccuucgg guuguaaacu gcuuuucugg gggaagagag aggacgguac ccaggaaga    420
agccccggca aacuacgugc cagcagccgc gguaagacgu agggggcgag cguugucccgg   480
```

```
aguuacuggg cguaaagggc cuguaggcgg ucgggcaggu uccggcggac agcccgcggc    540
uucacugcgg gagcagcagg aagacggcuc gacuugaggg ccacagaggg acauggaauu    600
cccgguggag cggugaaaug cguagagauc gggaagaaca ccgaaggcga aggcaguguc    660 cugggguggua ccugacgcug agaggcgaaa gcuaggggag cgaacgggau uagauacccc   720
gguaguccua gccguaaacg cugaccacua ggugguguggg gagaucgacc cccugcgcgc   780
cgaagcgaac gcaugaagug guccgccugg ggaguacggc cgcaaggcua aaacucaaag    840
gaauugacgg ggacccgcac aagcagcgga gcgugugguu uaauucgaug caacgcgaag    900
aaccuuacca ggguuggaca ugcgcgcuga ggguccagag augggccggc ccgcaaggga    960
ggcgcgcaca ggugcugcau ggcugucguc agcucgugcc gugaggguguu ggguuaaguc  1020 ccgcaacgag cgcaacccuc gcucucgguu ggauguguguc gagggggacug ccgcgcacaa 1080 cgcggaggaa ggugggggaug acgucaaguc agcauggccc ugacauccug ggcgacacac 1140
acgcuacaau ggucgggaca gcgggcagcg acccggcgac ggggagccaa ucccucaaac  1200
ccgaucucag ugcagauugc aggcugcaac ccgccugcau gaaggaggag uugcuaguaa  1260
ccgccgguca gcacacggcg gugaauacgu ucucgggucu uguacacacc gcccgucaca  1320
ccacgaaagc cggcaacacc ugaagccgcu gggcgaaccc cucgugagag gggaggcagg  1380
cgucga                                                             1386
```